United States Patent [19]

Scartazzini et al.

[11] 4,172,832

[45] Oct. 30, 1979

[54] MERCAPTOALCOHOLS AND PROCESS FOR THEIR MANUFACTURE

[75] Inventors: Riccardo Scartazzini, Allschwil; Hans Bickel, Binningen; Karl Heusler, Basel, all of Switzerland

[73] Assignee: Ciba-Geigy Corporation, Ardsley, N.Y.

[21] Appl. No.: 423,849

[22] Filed: Dec. 11, 1973

Related U.S. Application Data

[63] Continuation-in-part of Ser. No. 188,510, Oct. 12, 1971, abandoned.

[30] Foreign Application Priority Data

| Oct. 27, 1970 [CH] | Switzerland | 15845/70 |
|---|---|---|
| Nov. 10, 1970 [CH] | Switzerland | 1633/70 |
| Mar. 4, 1971 [CH] | Switzerland | 3197/71 |
| May 25, 1971 [CH] | Switzerland | 7608/71 |

[51] Int. Cl.$^2$ .................................. C07D 205/08
[52] U.S. Cl. .................. 260/239 A; 260/239.1; 260/245.2; 260/245.4
[58] Field of Search ........................ 260/239 A

[56] References Cited

U.S. PATENT DOCUMENTS

| 3,487,070 | 12/1969 | Sheehan | 260/239 A |
|---|---|---|---|
| 3,679,676 | 7/1972 | Heusler et al. | 260/239 A |
| 3,703,512 | 11/1972 | Heusler et al. | 260/239 A |
| 3,705,160 | 12/1972 | Heusler et al. | 260/239 A |
| 3,755,342 | 8/1973 | Heusler et al. | 260/239 A |
| 3,799,938 | 3/1974 | Heusler et al. | 260/239 A |
| 3,801,567 | 4/1974 | Heusler et al. | 260/239 A |

OTHER PUBLICATIONS

Ager et al., Chem. Comm., 1972, p. 601.
Jones et al., J. Amer. Chem. Soc., 60, pp. 2452–2455, (1938).
Plerson et al., J. Amer. Chem. Soc., 70, pp. 1450–1451, (1948).
Kalutskii et al., Chem. Abs. 69, 67099g, (1968).

*Primary Examiner*—Mark L. Berch
*Attorney, Agent, or Firm*—John J. Maitner

[57] ABSTRACT

The invention concerns 3-amino-4-(2-hydroxyethylthio)-2-oxo-azetidine compounds of the formula

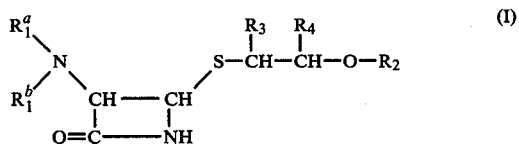

(I)

wherein $R_1^a$ represents hydrogen or an amino protective group $R_1^A$, $R_1^b$ represents hydrogen or an acyl group $Ac_1$, or $R_1^a$ and $R_1^b$ together denote a bivalent amino protective group, $R_2$ represents hydrogen or an acyl radical $Ac_2$, and each of the radicals $R_3$ and $R_4$ represents hydrogen or an organic radical bonded via a carbon atom, or salts of such compounds having salt-forming groups.

1 Claim, No Drawings

MERCAPTOALCOHOLS AND PROCESS FOR THEIR MANUFACTURE

CROSS-REFERENCE TO RELATED APPLICATION

This application is a continuation-in-part of our application Ser. No. 188,510, filed Oct. 12, 1971 (now abandoned).

The present invention relates to 3-amino-4-(2-hydroxyethylthio)-2-oxo-azetidine compounds of the formula

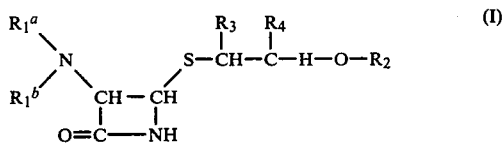

wherein $R_1{}^a$ represents hydrogen or an amino protective group $R_1{}^A$, $R_1{}^b$ represents hydrogen or an acyl group $Ac_1$, or $R_1{}^A$ and $R_1{}^b$ together denote a divalent amino protective group, $R_2$ represents hydrogen or an acyl radical $Ac_2$, and each of the radicals $R_3$ and $R_4$ represents hydrogen or an organic radical bonded via a carbon atom, or salts of such compounds which have salt-forming groups.

An amino protective group $R_1{}^A$ is a group replaceable by hydrogen, above all an acyl group $Ac_1$, and also a triarylmethyl group, especially the trityl group, or an organic silyl group or an organic stannyl group. A group Ac above all represents the acyl radical of an organic carboxylic acid or sulphonic acid, especially the acyl radical of an optionally substituted aliphatic, cycloaliphatic, cycloaliphatic-aliphatic, aromatic, araliphatic, heterocyclic or heterocyclic-aliphatic carboxylic acid (including formic acid) as well as the acyl radical of a carbonic acid half-derivative.

A bivalent amino protective group formed by the radicals $R_1{}^A$ and $R_1{}^b$ together is in particular the bivalent acyl radical of an organic dicarboxylic acid, above all the diacyl radical of an aliphatic or aromatic dicarboxylic acid, or the acyl radical of an α-aminoacetic acid which is preferably substituted in the α-position and, for example, contauns an aromatic or heterocyclic radical, in which α-aminoacetic acid the amino group is bonded to the nitrogen atom via a methylene radical which is preferably substituted and, for example, contains two lower alkyl groups, such as methyl groups. The radicals $R_1{}^A$ and $R_1{}^b$ can also together represent an organic ylidene radical, such as an aliphatic, cycloaliphatic, cycloaliphatic-aliphatic or araliphatic ylidene radical.

An acyl radical $Ac_2$ is above all the acyl radical of an organic carboxylic acid, especially an acyl radical of a carbonic acid half-derivative which is easily replaceable by hydrogen.

An organic radical bonded via a carbon atom is above all an optionally substituted hydrocarbon radical, especially an optionally substituted aliphatic, or cycloaliphatic, cycloaliphatic-aliphatic, aromatic or araliphatic hydrocarbon radical. At the same time at least one of the radicals $R_3$ and $R_4$, usually at least $R_3$ represents hydrogen.

The general terms used in the preceding and subsequent description for example have the following meanings:

An aliphatic radical, including the aliphatic radical of a corresponding organic carboxylic acid, and a corresponding ylidene radical, is an optionally substituted monovalent or divalent aliphatic hydrocarbon radical, especially lower alkyl, and also lower alkenyl or lower alkinyl, as well as lower alkylidene, which can, for example, contain up to 7, preferably up to 4, carbon atoms. Such radicals can optionally be monosubstituted, disubstituted or polysubstituted by functional groups, for example by free, etherified or esterified hydroxyl or mercapto groups, such as lower alkoxy, lower alkenyloxy, lower alkylenedioxy, optionally substituted phenyloxy or phenyl-lower alkoxy, lower alkylthio or optionally substituted phenylthio or phenyl-lower alkylthio, lower alkoxycarbonyloxy or lower alkanoyloxy, or halogen, and also by oxo, nitro, optionally substituted amino, for example di-lower alkylamino, lower alkyleneamino, oxa-lower alkyleneamino or aza-lower alkyleneamino, and also acylamino, such as lower alkanoylamino, optionally substituted carbamoylamino, ureidocarbonylamino or guanidinocarbonylamino, azido, acyl, such as lower alkanoyl or benzoyl, optionally functionally modified carboxyl, such as carboxyl present in the salt form, esterified carboxyl, such as lower alkoxycarbonyl, optionally substituted carbamoyl, such as N-lower alkylcarbamoyl or N,N-di-lower alkylcarbamoyl, and also optionally substituted ureidocarbonyl or guanidinocarbonyl, or cyano or optionally functionally modified sulpho, such as sulphamoyl or sulpho present in the salt form.

The bivalent aliphatic radical of an aliphatic carboxylic acid is, for example, lower alkylene or lower alkenylene, which can optionally be monosubstituted, disubstituted or polysubstituted, for example like an aliphatic radical mentioned above.

A cycloaliphatic or cycloaliphatic-aliphatic radical, including the cycloaliphatic or cycloaliphatic-aliphatic radical in a corresponding organic carboxylic acid or a corresponding cycloaliphatic or cycloaliphatic-aliphatic ylidene radical is an optionally substituted, monovalent or bivalent, cycloaliphatic or cycloaliphatic-aliphatic hydrocarbon radical, for example monocyclic, bicyclic or polycyclic cycloalkyl or cycloalkenyl as well as cycloalkylidene, or cycloalkyl- or cycloalkenyl-lower alkyl or -lower alkenyl, or cycloalkyl-lower alkylidene or cycloalkenyl-lower alkylidene, wherein cycloalkyl and cycloalkylidene for example contain up to 12, such as 3–8, preferably 3–6, ring carbon atoms, whilst cycloalkenyl for example possesses up to 12, such as 3–8, for example 5–8, preferably 5 or 6, ring carbon atoms and 1 to 2 double bonds, and the aliphatic part of a cycloaliphatic-aliphatic radical can, for example, contain up to 7, preferably up to 4, carbon atoms. The above cycloaliphatic or cycloaliphatic-aliphatic radicals can, if desired, be monosubstituted, disubstituted or polysubstituted, for example by optionally substituted aliphatic hydrocarbon radicals, such as by the above-mentioned optionally substituted lower alkyl groups, or, for example like the abovementioned aliphatic hydrocarbon radicals, by functional groups.

The aromatic radical, including the aromatic radical of a corresponding carboxylic acid, is an optionally substituted aromatic hydrocarbon radical, for example a monocyclic, bicyclic or polycyclic aromatic hydrocarbon radical, especially phenyl, as well as biphenylyl or naphthyl, which can optionally be monosubstituted, disubstituted or polysubstituted, for example like the abovementioned aliphatic and cycloaliphatic hydrocarbon radicals.

The divalent aromatic radical of an aromatic carboxylic acid is above all 1,2-arylene, especially 1,2-phenylene, which can optionally be monosubstituted, disubstituted or polysubstituted, for example like the abovementioned aliphatic and cycloaliphatic hydrocarbon radicals.

The araliphatic radical, including the araliphatic radical in a corresponding carboxylic acid, and also an araliphatic ylidene radical is, for example, an optionally substituted araliphatic hydrocarbon radical, such as an aliphatic hydrocarbon radical which is optionally substituted, for example possessing up to three optionally substituted monocyclic, bicyclic or polycyclic aromatic hydrocarbon radicals, and above all represents phenyl-lower alkyl or phenyl-lower alkenyl, as well as phenyl-lower alkinyl and also phenyl-lower alkylidene, and these radicals for example contain 1–3 phenyl groups and can optionally be monosubstituted, disubstituted or polysubstituted in the aromatic and/or aliphatic part, for example like the abovementioned aliphatic and cycloaliphatic radicals.

Heterocyclic groups, including those in heterocyclic-aliphatic radicals, including heterocyclic or heterocyclic-aliphatic groups in corresponding carboxylic acids, are especially monocyclic, as well as bicyclic or polycyclic, azacyclic, thiacyclic, oxacyclic, thiazacyclic, thiadiazacyclic, oxazacyclic, diazacyclic, triazacyclic or tetrazacyclic radicals of aromatic character, and also corresponding partially or wholly saturated radicals, and these heterocyclic radicals can optionally be monosubstituted, disubstituted or polysubstituted, for example like the abovementioned cycloaliphatic radicals. The aliphatic part in heterocyclic-aliphatic radicals for example has the meaning indicated for the corresponding cycloaliphatic-aliphatic or araliphatic radicals.

The acyl radical of a carbonic acid half-derivative is preferably the acyl radical of a corresponding half-ester, wherein the organic radical of the ester group represents an optionally substituted aliphatic, cycloaliphatic, aromatic or araliphatic hydrocarbon radical or a heterocyclic-aliphatic radical, above all the acyl radical of a lower alkyl half-ester of carbonic acid which is optionally substituted, for example in the α- or β-position, as well as a lower alkenyl, cycloalkyl, phenyl or phenyl-lower alkyl half-ester of carbonic acid which is optionally substituted in the organic radical. Acyl radicals of a carbonic acid half-ester are furthermore corresponding radicals of lower alkyl half-esters of carbonic acid, in which the lower alkyl part contains a heterocyclic group, for example one of the abovementioned heterocyclic groups of aromatic character, and in these acyl radicals both the lower alkyl radical and the heterocyclic group can optionally be substituted. The acyl radical of a carbonic acid half-derivative can also be an optionally N-substituted carbamoyl group, such as an optionally halogenated N-lower alkylcarbamoyl group.

Lower alkyl is, for example, methyl, ethyl, n-propyl, isopropyl, n-butyl, isobutyl, sec.-butyl or tert.-butyl as well as n-pentyl, isopentyl, n-hexyl, isohexyl or n-heptyl, whilst lower alkenyl can, for example, be vinyl, allyl, isopropenyl, 2- or 3-methallyl or 3-butenyl, lower alkinyl can, for example, be propargyl or 2-butinyl, and lower alkylidene can, for example, be isopropylidene or isobutylidene.

Lower alkylene is, for example, 1,2-ethylene, 1,2- or 1,3-propylene or 1,4-butylene, whilst lower alkenylene is, for example, 1,2-ethenylene or buten-1,4-ylen.

Cycloalkyl is, for example, cyclopropyl, cyclobutyl, cyclopentyl, cyclohexyl or cycloheptyl as well as adamantyl, cycloalkenyl is, for example, 2-cyclopropenyl, 1-, 2- or 3-cyclopentenyl, 1-, 2- or 3-cyclohexenyl, 3-cycloheptenyl or 1,4-cyclohexadienyl and cycloalkylidene is, for example, cyclopentylidene or cyclohexylidene. Cycloalkyl-lower alkyl or cycloalkyl-lower alkenyl is, for example, cyclopropyl-, cyclopentyl-, cyclohexyl- or cycloheptyl-methyl, -1,1- or 1,2-ethyl, -1,1-, -1,2- or -1,3-propyl, -vinyl or -allyl, whilst cycloalkenyl-lower alkyl or cycloalkenyl-lower alkenyl for example represents 1-, 2- or 3-cyclopentenyl-, 1-, 2- or 3-cyclohexenyl- or 1-, 2- or 3-cycloheptenylmethyl, -1,1- or -1,2-ethyl, -1,1-, -1,2- or -1,3-propyl, -vinyl or -allyl. Cycloalkyl-lower alkylidene is, for example, cyclohexylmethylene, and cycloalkenyl-lower alkylidene is, for example 3-cyclohexenylmethylene.

Naphthyl is 1- or 2-naphthyl, whilst biphenylyl for example represents 4-biphenylyl.

Phenyl-lower alkyl or phenyl-lower alkenyl is, for example, benzyl, 1- or 2-phenylethyl, 1-, 2- or 3-phenylpropyl, diphenylmethyl, trityl, 1- or 2-naphthylmethyl, styryl or cinnamyl and phenyl-lower alkylidene is, for example, benzylidene.

Heterocyclic radicals are above all optionally substituted heterocyclic radicals of aromatic character, for example appropriate monocyclic, monoazacyclic, monothiacyclic or monooxacyclic radicals, such as pyrryl, for example 2-pyrryl or 3-pyrryl, pyridyl, for example 2-, 3- or 4-pyridyl, as well as pyridinium, thienyl, for example 2- or 3-thienyl, or furyl, for example 2-furyl, bicyclic monoazacyclic, monooxacyclic or monothiacyclic radicals, such as indolyl, for example 2- or 3-indolyl, quinolinyl, for example 2- or 4-quinolinyl, isoquinolinyl, for example 1-isoquinolinyl, benzofuranyl, for example 2- or 3-benzofuranyl, or benzothienyl, for example 2- or 3-benzothienyl, monocyclic diazacyclic, triazacyclic, tetrazacyclic, thiazacyclic, thiadiazacyclic or oxazacyclic radicals, such as imidazolyl, for example 2-imidazolyl, pyrimidinyl, for example 2- or 4-pyrimidinyl, triazolyl, for example 1,2,4-triazol-3-yl, tetrazolyl, for example 1- or 5-tetrazolyl, oxazolyl, for example 2-oxazolyl, isoxazolyl, for example 3-isoxazolyl, thiazolyl, for example 2-thiazolyl, isothiazolyl, for example 3-isothiazolyl or 1,2,4- or 1,3,4-thiadiazolyl, for example 1,2,4-thiadiazol-3-yl or 1,3,4-thiadiazol-2-yl, or bicyclic diazacyclic, thiazacyclic or oxazacyclic radicals, such as benzimidazolyl, for example 2-benzimidazolyl, benzoxazolyl, for example 2-benzoxazolyl, or benzthiazolyl, for example 2-benzthiazolyl. Appropriate partially or wholly saturated radicals are, for example, tetrahydrothienyl, such as 2-tetrahydrothienyl, tetrahydrofuryl, such as 2-tetrahydrofuryl, or piperidyl, for example 2- or 4-piperidyl. Heterocyclic-aliphatic radicals are lower alkyl or lower alkenyl containing heterocyclic groups, especially those mentioned above. The abovementioned heterocyclyl radicals can, for example be substituted by optionally substituted aliphatic hydrocarbon radicals, especially lower alkyl, such as methyl, or, for example like the aliphatic hydrocarbon radicals, by functional groups.

Lower alkoxy is, for example, methoxy, ethoxy, n-propoxy, isopropoxy, n-butoxy, isobutoxy, sec.-butoxy, tert.-butoxy, n-pentyloxy or tert.-pentyloxy. These groups can be substituted, for example as in halogeno-lower alkoxy, especially 2-halogeno-lower alkoxy, for example 2,2,2-trichloroethoxy, 2-bromoethoxy or 2-iodoethoxy. Lower alkenyloxy is, for example, vinyloxy or allyloxy, lower alkylenedioxy is, for example, methylenedioxy, ethylenedioxy or isopropylidenedioxy, cycloalkoxy is, for example, cyclopentyloxy, cyclohexyloxy or adamantyloxy, phenyl-lower alkoxy is, for example, benzyloxy or 1- or 2-phenylethoxy, or heterocyclyloxy or heterocyclyl-lower alkoxy is, for example, pyridyl-lower alkoxy, such as 2-pyridylmethoxy, furyl-lower alkoxy, such as furfuryloxy, or thienyl-lower alkoxy, such as 2-thenyloxy.

Lower alkylthio is, for example, methylthio, ethylthio, or n-butylthio, lower alkenylthio is, for example, allylthio, and phenyl-lower alkylthio is, for example, benzylthio, whilst mercapto groups etherified by heterocyclyl radicals or by heterocyclyl-aliphatic radicals are in particular imidazolylthio, for example 2-imidazolylthio, thiazolylthio, for example 2-thiazolylthio, 1,2,4- or 1,3,4-thiadiazolylthio, for example 1,2,4-thiadiazol-3-ylthio or 1,3,4-thiadiazol-2-ylthio, or tetrazolylthio, for example 1-methyl-5-tetrazolylthio.

Esterified hydroxyl groups are above all halogen, for example fluorine, chlorine, bromine or iodine, and lower alkanoyloxy, for example acetoxy or propionyloxy.

Lower alkoxycarbonyl is, for example, methoxycarbonyl, ethoxycarbonyl, n-propoxycarbonyl, isopropoxycarbonyl, tert.-butoxycarbonyl or tert.-pentyloxycarbonyl.

N-lower alkyl-carbamoyl or N,N-di-lower alkylcarbamoyl is, for example, N-methylcarbamoyl, N-ethylcarbamoyl, N,N-dimethylcarbamoyl or N,N-diethylcarbamoyl, whilst N-lower alkylsulphamoyl for example represents N-methylsulphamoyl or N,N-dimethylsulphamoyl.

A carboxyl group or sulpho group present in the alkali metal salt formed is, for example, a carboxyl or sulpho group present in the form of a sodium salt is potassium salt.

Lower alkylamino or di-lower alkylamino is, for example, methylamino, ethylamino, dimethylamino or diethylamino, lower alkyleneamino is, for example, pyrrolidino or piperidino, oxa-lower alkyleneamino is, for example, morpholino and aza-lower alkyleneamino is, for example, piperazino or 4-methylpiperazino. Acylamino in particular represents carbamoylamino, lower alkylcarbamoylamino, such as methylcarbamoylamino, ureidocarbonylamino, guanidinocarbonylamino, lower alkanoylamino, such as acetylamino or propionylamino, and also phthalimido, or sulphoamino which is optionally present in the salt form, such as the form of an alkali metal salt, for example sodium salt, or the form of an ammonium salt.

Lower alkanoyl is, for example, acetyl or propionyl.

Lower alkenyloxycarbonyl is, for example, vinyloxycarbonyl, whilst cycloalkoxycarbonyl and phenyl-lower alkoxycarbonyl for example represent adamantyloxycarbonyl, benzyloxycarbonyl, diphenylmethoxycarbonyl or α-4-biphenylyl-α-methyl-ethoxycarbonyl. Lower alkoxycarbonyl, wherein lower alkyl for example contains a monocyclic, monoazacyclic, monooxacyclic, or monothiacyclic group, is, for example, furyl-lower alkoxycarbonyl, such as furfuryloxycarbonyl or thienyl-lower alkoxycarbonyl, for example, 2-thenyloxycarbonyl.

An acyl group Ac$_1$ in particular represents an acyl radical of an organic carboxylic acid, or of a carbonic acid half-derivative, contained in a naturally occurring or a biosynthesisable, semi-synthesisable or totally synthesisable, preferably pharmacologically active, N-acyl derivative of 6-amino-penicillanic acid or 7-amino-cephalosporanic acid compounds, or represents an easily removable acyl radical of a carbonic acid half-derivative.

An acyl radical Ac$_1$ contained in pharmacologically active N-acyl derivatives of 6-amino-penicillanic acid or 7-amino-cephalosporanic acid is above all a group of the formula

(IA)

wherein n represents 0 and $R^I$ denotes hydrogen or an optionally substituted cycloaliphatic or aromatic hydrocarbon radical, or an optionally substituted heterocyclic radical, preferably of aromatic character, a functionally modified, preferably etherified, hydroxyl or mercapto group or an optionally substituted amino group, or wherein n represents 1, $R^I$ represents hydrogen or an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably is of aromatic character and/or possesses quaternary nitrogen atom, an optionally functionally modified, preferably etherified or esterified, hydroxyl or mercapto group, an optionally functionally modified carboxyl group, an acyl group, an optionally substituted amino group or an azido group, and each of the radicals $R^{II}$ and $R^{III}$ denote hydrogen, or wherein n represents 1, $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein the heterocyclic radical preferably possesses aromatic character, $R^{II}$ denotes an optionally functionally modified, preferably etherified, hydroxyl or mercapto group, an optionally substituted amino group, an optionally functionally modified carboxyl group or a sulpho group, an azido group or a halogen atom, and $R^{III}$ represents hydrogen, or wherein n represents 1, each of the radicals $R^I$ and $R^{II}$ denotes a functionally modified, preferably etherified or esterified, hydroxyl group or an optionally functionally modified carboxyl group, and $R^{III}$ represents hydrogen, or wherein n represents 1, $R^I$ denotes hydrogen or an optionally substituted aliphatic, cycloaliphatic, cycloaliphatic-aliphatic, aromatic or araliphatic hydrocarbon radical and $R^{II}$ and $R^{III}$ together represent an optionally substituted aliphatic, cycloaliphatic, cycloaliphatic-aliphatic or araliphatic hydrocarbon radical which is bonded to the carbon atom by a double bond, or wherein n represents 1 and $R^I$ denotes an optionally substituted aliphatic, cycloaliphatic, cycloaliphatic-aliphatic, aromatic or araliphatic hydrocarbon radical or an optionally substituted heterocyclic or heterocyclic-aliphatic radical, wherein heterocyclic radicals preferably are of aromatic character, $R^{II}$ denotes an optionally substituted aliphatic, cycloaliphatic, cycloaliphatic-aliphatic, aromatic or araliphatic hydrocarbon radical and $R^{III}$ denotes hydrogen or an optionally substituted aliphatic, cycloaliphatic, cycloaliphatic-aliphatic, aromatic or araliphatic hydrocarbon radical.

In the abovementioned acyl groups of the formula IA, n for example represents O and $R^I$ represents hydrogen or a cycloalkyl group with 5–7 ring carbon atoms which is optionally substituted, preferably in the 1-position, by amino or a sulphoamino group which is optionally present in the salt form, for example the form of an alkali metal salt, a phenyl, naphthyl or tetrahydronaphthyl group which is optionally substituted, preferably by hydroxyl, lower alkoxy, for example methoxy and/or halogen, for example chlorine, a heterocyclic group, such as a 4-isoxazolyl group, which is optionally substituted, for example by lower alkyl, e.g. methyl and/or phenyl, which can in turn carry substituents, such as halogen, for example chlorine, or an amino group which is preferably N-substituted, for example by an optionally substituted lower alkyl radical, such as a lower alkyl radical containing halogen, for example chlorine, or n represents 1, $R^I$ represents a lower alkyl group which is optionally substituted, preferably by halogen, such as chlorine, by optionally substituted phenyloxy, such as phenyloxy containing hydroxyl and/or halogen, for example chlorine, by amino and/or by carboxyl, a lower alkenyl group, an optionally substituted phenyl group, such as a phenyl group containing hydroxyl, halogen, for example chlorine and/or optionally substituted phenyloxy, a pyridyl, pyridinium, thienyl, 1-imidazolyl or 1-tetrazolyl group which is optionally substituted, for example by amino or aminomethyl, an optionally substituted lower alkoxy group, a phenyloxy group which is optionally substituted, for example by hydroxyl and/or halogen, such as chlorine, a lower alkylthio or lower alkenylthio group, an optionally substituted, for example lower alkyl-substituted, such as methyl-substituted, phenylthio, 2-imidazolylthio, 1,2,4-triazol-3-ylthio, 1,3,4-triazol-2-ylthio, 1,2,4-thiadiazol-3-ylthio, such as 5-methyl-1,2,4-thiadiazol-3-ylthio, 1,3,4-thiadiazol-2-ylthio, such as 5-methyl-1,3,4-thiadiazol-2-ylthio, or 5-tetrazolylthio, such as 1-methyl-5-tetrazolylthio group, a halogen atom, especially a chlorine or bromine atom, an optionally functionally modified carboxyl group, such as a lower alkoxycarbonyl group, cyano group, or carbamoyl group which is optionally N-substituted, for example by phenyl, an optionally substituted lower alkanoyl or benzoyl group, or an azido group, and $R^{II}$ and $R^{III}$ represent hydrogen, or n represents 1, $R^I$ represents a phenyl or thienyl group which is optionally substituted, for example by hydroxyl and/or halogen, for example chlorine, or represents a 1,4-cyclohexadienyl group, $R^{II}$ represents an optionally substituted amino group, for example an optionally substituted carbamoylamino group, such as guanidinocarbonylamino, or a sulphoamino group optionally present in the salt form, for example the form of an alkali metal salt, an azido group, a carboxyl group which is optionally present in the salt form, for example the form of an alkali metal salt, or in an esterified form, such as a lower alkoxycarbonyl group, a cyano group, a sulpho group, an optionally substituted lower alkoxy or phenyloxy group or a halogen, e.g. chlorine or bromine atom, and $R^{III}$ represents hydrogen, or n represents 1, $R^I$ and $R^{II}$ each represent halogen, for example bromine, or lower alkoxycarbonyl, for example methoxycarbonyl, and $R^{III}$ represents hydrogen, or n represents 1 and each of the groups $R^I$, $R^{II}$ and $R^{III}$ represent lower alkyl, for example methyl.

Such acyl radicals are, for example, formyl, cyclopentylcarbonyl, α-aminocyclopentylcarbonyl or α-aminocyclohexylcarbonyl (with an optionally substituted amino group, for example a sulphoamino group which is optionally present in the salt form, or an amino group which is substituted by an acyl radical which can be split off, preferably easily, for example on treatment with an acid agent, such as trifluoroacetic acid, or with a chemical reducing agent, such as zinc in the presence of aqueous acetic acid, or which is substituted by an acyl radical which can be converted into such a radical, preferably a suitable acyl radical of a carbonic acid half-ester, such as 2,2,2-trichloroethoxycarbonyl, 2-bromoethoxycarbonyl, 2-iodoethoxycarbonyl, tert.-butoxycarbonyl or phenacyloxycarbonyl, or of a carbonic acid half-amide, such as carbamoyl or N-methylcarbamoyl), 2,6-dimethoxybenzoyl, tetrahydronaphthoyl, 2-methoxy-naphthoyl, 2-ethoxy-naphthoyl, benzyloxycarbonyl, hexahydrobenzyloxycarbonyl, 5-methyl-3-phenyl-4-isoxazolylcarbonyl-, 3-(2-chlorophenyl)-5-methyl-4-isoxazolylcarbonyl, 3-(2,6-dichlorophenyl)-5-methyl-4-isoxazolylcarbonyl, 2-chloroethylaminocarbonyl, acetyl, propionyl, butyryl, hexanoyl, octanoyl, acrylyl, crotonoyl, 3-butenoyl, 2-pentenoyl, methoxyacetyl, methylthioacetyl, butylthioacetyl, allylthioacetyl, chloroacetyl, bromoacetyl, dibromoacetyl, 3-chloropropionyl, 3-bromopropionyl, aminoacetyl or 5-amino-5-carboxyl-valeryl (with an amino group which is optionally substituted, for example as indicated, and/or a carboxyl group which is optionally functionally modified, for example which is present in the salt form, such as the form of the sodium salt, or in the ester form, such as in the form of a lower alkyl ester, for example the form of the methyl ester or ethyl ester), azidoacetyl, carboxyacetyl, methoxycarbonylacetyl, ethoxycarbonylacetyl, bismethoxycarbonylacetyl, N-phenylcarbamoylacetyl, cyanoacetyl, α-cyanopropionyl, 2-cyano-3,3-dimethylacrylyl, phenylacetyl, α-bromophenylacetyl, α-azido-phenylacetyl, 3-chlorophenylacetyl, 4-aminomethylphenyl-acetyl (with an amino group which is optionally substituted, for example as indicate above), phenacylcarbonyl, phenyloxyacetyl, 4-trifluoromethyl-phenyloxyacetyl, benzyloxyacetyl, phenylthioacetyl, bromophenylthioacetyl, 2-phenyloxypropionyl, α-phenyloxyphenylacetyl, α-methoxyphenylacetyl, α-ethoxy-phenylacetyl, α-methoxy-3,4-dichlorophenylacetyl, α-cyano-phenylacetyl, and especially phenylglycyl, 4-hydroxy-phenylglycyl, 3-chloro-4-hydroxyphenylglacyl or 3,5-dichloro-4-hydroxyphenylglycyl (whereby these residues have amino groups which are optionally substituted, for example as indicated above), furthermore, benzylthioacetyl, benzylthiopropionyl, α-carboxy phenylacetyl (with a carboxyl group which is optionally function ally modified, for example as indicated above), 3-phenylpropionyl. 3-(3-cyanophenyl)-propionyl, 4-(3-methoxyphenyl)-butyryl, 2-pyridylacetyl, 4-aminopyridiniumacetyl (optionally with an amino group which is substituted, for example as indicated above), 2-thienylacetyl, 2-tetrahydrothienylacetyl, α-carboxy-2-thienylacetyl or α-carboxy-3-thienylacetyl (optionally with a carboxyl group which is functionally modified, for example as indicated above), α-cyano-2-thienylacetyl, α-amino-2-thienylacetyl or α-amino-3-thienylacetyl (optionally with an amino group which is substituted, for example as indicated above), α-sulpho-phenylacetyl (optionally with a sulpho group which is functionally modified, for example like a carboxyl group), 3-thienylacetyl, 2-furylacetyl, 1-imidazolylacetyl, 1-tetrazolylacetyl, 3-methyl-2-imidazolyl-thioacetyl, 1,2,4-triazol-3-ylthioacetyl, 1,3,4-triazol-2-ylthioacetyl, 5-methyl-1,2,4-thiadiazol-3-ylthioacetyl, 5-methyl-1,3,4-thiadiazol-2-ylthioacetyl or 1-methyl-5-tetrazolylthioacetyl.

An easily removable acyl radical $Ac_1$ is especially the acyl radical of a carbonic acid half-ester and above all an acyl radical of a half-ester of carbonic acid which can be split off by reduction, for example on treatment with a chemical reducing agent, or by treatment with acid, for example with trifluoroacetic acid, such as a lower alkoxycarbonyl radical which is preferably branched several-fold in the α-position or is substituted by acylcarbonyl, especially benzoyl, radicals, or is substituted in the β-position by halogen atoms, for example tert.-butoxycarbonyl, tert.-pentyloxycarbonyl, phenacyloxycarbonyl, 2,2,2-trichloroethoxycarbonyl or 2-iodoethoxycarbonyl or a radical which can be converted into the latter, such as 2-chloroethoxycarbonyl or 2-bromoethoxycarbonyl, and also preferably polycyclic cycloalkoxycarbonyl, for example adamantyloxycarbonyl, optionally substituted phenyl-lower alkoxycarbonyl, above all α-phenyl-lower alkoxycarbonyl, wherein the α-position preferably is substituted several-fold, for example diphenylmethoxycarbonyl or α-4-biphenylyl-α-methyl-ethoxycarbonyl, a furyl-lower alkoxycarbonyl, above all α-furyl-lower alkoxycarbonyl, for example furfuryloxycarbonyl.

Organic radicals $R_3$ and $R_4$ are above all optionally substituted aliphatic hydrocarbon radicals, such as lower alkyl radicals optionally substituted by halogen, and also phenyl-lower alkyl groups.

An acyl group $Ac_2$ above all represents an esterified carboxyl group of the formula $-C(=O)-X_1$ which can be split under mild conditions, wherein $X_1$ for example represents the radical of the formula $-O-R_2^a$, which together with the carbonyl group forms an esterified carboxyl group which can easily be split on treatment with chemical reducing agents under neutral or weakly acid conditions. In this group, $R_2^a$ denotes a 2-halogeno-lower alkyl radical in which halogen preferably has an atomic weight of above 19, especially a 2-polychloro-lower alkyl radical, such as a 2-polychloroethyl radical, above all the 2,2,2-trichloroethyl radical, or the 2,2,2-trichloro-1-methyl-ethyl radical, but can also denote, for example, a 2-bromo-lower alkyl radical, such as a 2-polybromo-lower alkyl radical, such as the 2,2,2-bromoethyl radical, and also the 2-bromoethyl radical, or a 2-iodo-lower alkyl radical, for example in particular the 2-iodoethyl radical.

A further group $X_1$ which together with the carbonyl grouping represents an esterified carboxyl group which can easily be split on treatment with chemical reducing agents under neutral or weakly acid conditions is the group $-O-R_2^b$, wherein $R_2^b$ represents an arylcarbonylmethyl group and preferably the unsubstituted phenacyl radical, or a phenacyl radical which is substituted in the aromatic part, such as a phenacyl radical substituted by lower alkyl or lower alkoxy groups or halogen atoms.

The group $X_1$ can also represent the radical of the formula $-O-R_2^c$, which together with the carbonyl grouping represents an esterified carboxyl group which can easily be split on irradiation under neutral or weakly acid conditions. In this group, $R_2^c$ represents an aryl-methyl group, wherein aryl denotes an optionally substituted phenyl group of which the substituents are above all functional groups, such as free or functionally modified carboxyl groups, for example carboxyl, lower alkoxycarbonyl, carbamoyl or nitrile groups, optionally substituted amino groups, such as di-lower alkylamino groups, or acyl groups, such as lower alkanoyl groups, but especially optionally functionally modified, especially esterified, hydroxyl or mercapto groups, such as acyloxy groups, for example lower alkanoyloxy groups, or halogen atoms, and above all etherified hydroxyl or mercapto groups, such as lower alkoxy groups, as well as lower alkylthio groups (which in the preferred phenyl radical are above all in the 3-, 4- and/or 5-position) and/or above all nitro groups (in the case of the preferred phenyl radical, preferably in the 2-position). Such groups $R_2^c$ are in particular 1-phenylethyl or benzhydryl, above all benzyl, radicals which are substituted by lower alkoxy groups, such as methoxy groups, preferably in the 3-, 4- and/or 5-position and/or by nitro groups, preferably in the 2-position, and in particular the 3- or 4-methoxybenzyl, 3,5-dimethoxy-benzyl, 2-nitrobenzyl or 4,5-dimethoxy-2-nitro-benzyl radical.

A group $X_1$ can also represent the radical of the formula $-O-R_2^d$, which together with the carbonyl grouping forms an esterified carboxyl group which can easily be split under acid conditions. Such a radical $R_2^d$ is above all a methyl group which is monosubstituted by a carbocyclic aryl group possessing electron-donating substituents or by a heterocyclic group of aromatic character possessing oxygen atoms or sulphur atoms as ring members or denotes, in an oxacycloaliphatic or thiacycloaliphatic radical, the ring member which represents the α-position to the oxygen atom or to the sulphur atom.

A carbocyclic aryl group containing electron-donating substituents in the aryl radical is above all the phenyl radical, suitable substituents, which are preferably in the p- and/or o-position of the phenyl radical, being, for example, free or preferably functionally modified, such as esterified and above all etherified, hydroxyl groups, such as lower alkoxy groups, and also corresponding free or functionally modified mercapto groups, as well as aliphatic, cycloaliphatic, aromatic or araliphatic, optionally suitably substituted, hydrocarbon radicals, especially lower alkyl groups, or aryl groups, for example phenyl groups.

A heterocyclic group of aromatic character containing oxygen or sulphur atoms as ring members is above all a furyl radical, for example a 2-furyl radical, or a thienyl radical, for example a 2-thienyl radical.

An oxacycloaliphatic and thiacycloaliphatic radical which is linked in the α-position is above all a 2-oxacycloalkyl or 2-thiacycloalkyl, as well as 2-oxacycloalkenyl or 2-thiacycloalkenyl, group, in which the methyl group $R_2^d$ represents the ring member adjacent to the ring oxygen atom or ring sulphur atom, and which preferably contains 4-6 ring carbon atoms, above all a 2-tetrahydrofuryl, 2-tetrahydropyranyl or 2,3-dihydro-2-pyranyl radical or a corresponding sulphur analogue.

Preferred radicals $R_2^d$ are 4-methoxybenzyl and 3,4-dimethoxybenzyl radicals, as well as 2-tetrahydrofuryl, 2-tetrahydropyranyl or 2,3-dihydro-2-pyranyl groups.

An esterified carboxyl group of the formula $-C(=O)-X_1$ which can also be split under acid conditions is the group of the formula $-C(=O)-O-R_2^e$, wherein $R_2^e$ preferably is a methyl radical which is substituted several-fold in the α-position, such as a lower alkyl group which is branched several-fold in the α-position, for example a tert.-butyl or tert.-pentyl group, a cycloalkyl group, for example an adamantyl group, a polyarylmethyl group, for example a benzhydryl or trityl group, or a 2-(4-biphenylyl)-1-methylethyl group.

A further easily splittable esterified carboxyl group of the formula —C(=O)—X$_1$ is a group of the formula —C(=O)—O—R$_2^f$, wherein R$_2^f$ represents an organic radical which together with the carboxyl group forms an esterified carboxyl group which can be split under hydrolytic conditions, such as an activated ester grouping and in particular denotes a cyanomethyl, 4-nitrophenyl, 4-nitrobenzyl, phthalimidomethyl or succinimidomethyl group.

Salts of compounds of the formula I are especially acid addition salts of those compounds, in which R$_1^a$ and R$_1^b$ represent hydrogen; suitable acids are above all inorganic acids, such as hydrogen halide acids, for example hydrochloric acid, hydrobromic acid or hydriodic acid, sulphuric acid or phosphoric acids, as well as strong organic carboxylic acids or sulphonic acids.

As indicated below, the compounds of the formula I represent valuable intermediate products for the manufacture of pharmacologically active compounds.

Particularly valuable intermediate products are compounds of the formula I, wherein R$_1^a$ denotes hydrogen or the acyl group Ac' which represents an acyl radical contained in a preferably pharmacologically active, fermentatively (i.e. naturally occurring) or synthetically obtainable N-acyl derivative of 6-amino-penicillanic acid compounds or 7-aminocephalosporanic acid compounds or represents an easily removable acyl radical of a carbonic acid half-derivative, R$_1^b$ denotes hydrogen, R$_2$ represents hydrogen or an easily removable acyl radical of the formula —C(=O)—X$_1$, wherein X$_1$ represents an etherified hydroxyl group which together with the carbonyl grouping denotes a carboxyl group which can be split under mild conditions, and each of the groups R$_3$ and R$_4$ denotes hydrogen or a lower alkyl radical, above all a methyl radical, which is optionally substituted, for example by free or functionally modified, such as etherified or esterified, hydroxyl or mercapto groups, for example lower alkoxy, lower alkylthio or lower alkanoyloxy groups or halogen atoms, or by optionally fuctionally modified carboxyl groups, such as lower alkoxycarbonyl, carbamyl or cyano groups, or a phenyl or phenyl-lower alkyl, for example benzyl radical which is optionally substituted, for example like the abovementioned lower alkyl radical or by lower alkyl radicals, R$_3$ preferably representing hydrogen.

In a compound of the formula I, R$_1^a$ above all represents hydrogen or an acyl radical contained in fermentatively (i.e. naturally occurring) or biosynthetically obtainable N-acyl derivatives of 6-amino-penam-3-carboxylic acid compounds or 7-amino-ceph-3-em-4-carboxylic acid compounds, such as an optionally substituted phenylacetyl or phenyloxyacetyl radical, as well as an optionally substituted lower alkanoyl or lower alkenoyl radical, for example 4-hydroxy-phenylacetyl, hexanoyl, actanoyl, 3-hexenoyl, 5-amino-5-carboxyvaleryl, n-butyl-thioacetyl or allylthioacetyl, and especially phenylacetyl or phenyloxyacetyl, an acyl radical occurring in highly active N-acyl derivatives of 6-amino-penam-3-carboxylic acid or 7-amino-ceph-3-em-4-carboxylic acid compounds, such as formyl, 2-chloroethylcarbamoyl, cyanoacetyl or 2-thienylacetyl, especially phenylglycyl wherein phenyl optionally represents phenyl which is substituted by hydroxyl and/or halogen, for example chlorine, for example phenyl or 3- or 4-hydroxyphenyl, 3-chloro-4-hydroxy-phenyl or 3,5-dichloro-4-hydroxyphenyl, and wherein the amino group is optionally substituted and for example represents a sulphoamino group optionally present in the salt form or represents an amino group which contains an optionally substituted carbamoyl groups, such as an optionally substituted ureido-carbonyl group, for example ureidocarbonyl or N$^3$-trichloromethylureidocarbonyl, or an optionally substituted guanidinocarbonyl group, for example guanidinocarbonyl, or an acyl radical which can be split off, preferably easily, for example on treatment with an acid agent, such as trifluoroacetic acid, or with a chemical reducing agent, such as zinc in the presence of aqueous acetic acid, or an acyl radical which can be converted into such an acyl radical, preferably a suitable acyl radical of a carbonic acid half-ester, such as 2,2,2-trichloroethoxycarbonyl, 2-chloroethoxycarbonyl, 2-bromoethoxycarbonyl, 2-iodoethoxycarbonyl, tert.-butoxycarbonyl or phenacyloxycarbonyl, or of a carbonic acid half-amide, such as carbamoyl or N-methylcarbamoyl, or an amino group which is linked with the nitrogen atom of the 3-amino group by a methylene group which is optionally substituted by lower alkyl, e.g. two methyl groups, and also thienylglycycl, such as 2-thienylglycyl (optionally with an amino group which is substituted, for example as indicated above), or 1-amino-cyclohexylcarbonyl (optionally with an amino group which is substituted, for example as indicated above), and also α-carboxy-phenylacetyl or α-carboxy-2-thienylacetyl (optionally with a functionally modified carboxyl group, for example a carboxyl group present in the salt form, such as the form of the sodium salt or in the ester form, such as the form of lower alkyl e.g. methyl or ethyl, or phenyl-lower alkyl, e.g. diphenylmethyl esters) or α-sulphoform, such as the form of lower alkyl esters) or α-sulphophenylacetyl (optionally with a sulpho group which is functionally modified, for example like the carboxyl group) or an acyl radical of a carbonic acid half-ester which can easily be split off, especially under acid conditions, for example on treatment with trifluoroacetic acid, or by reduction, for example with zinc in the presence of aqueous acetic acid, such as tert.-butoxycarbonyl, phenacylcarbonyl, 2,2,2-trichloroethoxycarbonyl or 2-iodoethoxycarbonyl or the 2-bromoethoxycarbonyl which can be converted into the latter, R$_1^b$ represents hydrogen and R$_2$ represents hydrogen or an acyl radical of a carbonic acid half-ester which can easily be split off, for example as indicated, such as a radical of the formula —C(=O)—O—R$_2^a$, —C(=O)—O—R$_2^b$ or —C(=O)—O—R$_2^e$, for example the tert.-butoxycarbonyl, 2,2,2-trichloroethoxycarbonyl or 2-iodoethoxycarbonyl radical or the 2-chloroethoxycarbonyl or 2-bromoethoxycarbonyl radical which can be converted into the latter, and also the phenacyloxycarbonyl radical, whilst R$_3$ denotes hydrogen and R$_4$ denotes above all hydrogen, as well as lower alkyl which is optionally substituted by halogen, for example fluorine, above all methyl or ethyl, furthermore phenyl-lower alkyl, especially benzyl.

The invention relates above all to compounds of the formula

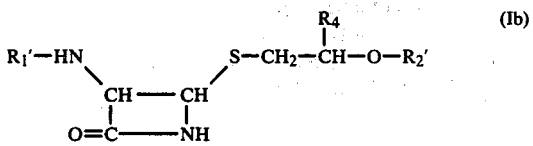

wherein $R_1'$ denotes hydrogen or an acyl group of the formula

wherein Ar represents phenyl, 3- or 4-hydroxy-phenyl, 3-chloro-4-hydroxy-phenyl, 3,5-dichloro-4-hydroxyphenyl or 2-thienyl, R represents hydrogen or amino, carboxyl or sulpho, which is preferably protected such as acylamino, e.g. tert.-butoxycarbonylamino, 2,2,2-trichloroethoxycarbonylamino, 2-bromoethoxycarbonylamino or 2-iodoethoxycarbonylamino, as well as esterified carboxy, e.g. diphenylmethoxycarbonyl, $R_2'$ denotes hydrogen or an acyl radical of the carbonic acid half-ester which is easily replaceable by hydrogen, such as 2,2,2-trichloroethoxycarbonyl, 2-chloroethoxycarbonyl, 2-bromoethoxycarbonyl, 2-iodoethoxycarbonyl, phenacyloxycarbonyl or tert.-butoxycarbonyl, and $R_4$ denotes hydrogen, lower alkyl, especially methyl, lower alkyl substituted by halogen, especially methyl substituted by halogen, above all fluoromethyl.

According to the invention, the mercaptoalcohol compounds of the formula I are obtained if a bis-(cis-3-N-$R_1^A$-N-$R_1^b$-amino-2-oxo-4-azetidinyl)-disulphide compound of the formula

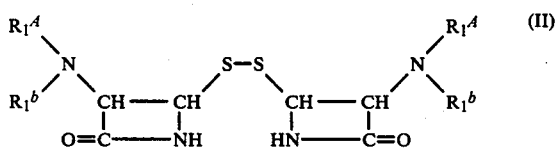

is reacted with an oxirane compound of the formula

with simultaneous treatment with a reducing agent and, if desired, in a resulting compound of the formula I, in which $R_2$ represents hydrogen, the hydroxy group is converted into an acyloxy group and/or, if desired in a compound obtainable the group $R_1^A$ and/or the radical representing an acyl group Ac or a bivalent amino protective group formed by $R_1^A$ and $R_1^b$ is split off and, if appropriate, in a compound thus obtainable the free amino group is protected and/or a resulting salt is converted into the free compound or into a different salt and/or a free compound is converted into a salt and/or, if desired, a resulting isomer mixture is separated into the individual isomers.

Reducing agents used are above all chemical reducing agents, for example suitable reducing metals, as well as reducing metal compounds, for example metal alloys or metal amalgams, and also strongly reducing metal salts. Zinc, zinc alloys, for example zinc-copper, or zinc amalgam, and also magnesium, are particulary suitable, and these are preferably used in the presence of hydrogen-releasing agents which together with the metals, metal alloys and metal amalgams are able to generate nascent hydrogen, zinc, for example, being used advantageously in the presence of acids, such as organic carboxylic acids, for example lower alkanecarboxylic acids, above all acetic acid, or of acid reagents, such as ammonium chloride or pyridine hydrochloride, preferably with the addition of water, or being used in the presence of alcohols, especially aqueous alcohols, such as lower alkanols, for example methanol, ethanol or isopropanol, which can optionally be used together with an organic carboxylic acid, and alkali metal amalgams, such as sodium amalgam or potassium amalgam, or aluminium amalgam, preferably being used in the presence of moist solvents, such as ethers or lower alkanols.

Strongly reducing metal salts are above all chromium-II compounds, for example chromium-II chloride or chromium-II acetate, which are preferably used in the presence of aqueous media containing organic solvents which are miscible with water, such as lower alkanols, carboxylic acids, such as lower alkanecarboxylic acids or derivatives, such as optionally substituted, for example lower alkylated, amides thereof, or ethers, for example methanol, ethanol, acetic acid, dimethylformamide, tetrahydrofurane, dioxane, ethylene glycol dimethyl ether or diethylene glycol dimethyl ether.

The reaction according to the invention is preferably carried out in the presence of a solvent, above all a solvent which is miscible with water, such as a lower alkanol, for example ethanol, an ether, for example tetrahydrofurane, or a lower alkanecarboxylic acid, for example acetic acid, or a solvent mixture, usually in the presence of water, and under mild conditions, usually at room temperature or with cooling, for example at about $-20°$ C. to about $+10°$ C., and if necessary also at elevated temperature, for example at temperatures up to about $100°$ C., and/or in a closed vessel and/or in an inert gas atmosphere, for example in a nitrogen atmosphere.

In a compound of the formula I obtainable according to the process, in which $R_2$ stands for hydrogen, the hydroxyl group can be acylated according to methods which are in themselves known, for example by treatment with carboxylic acids or reactive acid derivatives thereof, such as halides, for example chlorides, anhydrides (by which term there are also to be understood the internal anhydrides of carboxylic acids, that is to say ketenes, or of carbamic acids or thiocarbamic acids, that is to say isocyanates or isothiocyanates, or mixed anhydrides, such as those which can be formed, for example, with chloroformic acid lower alkyl esters or trichloroacetic acid chloride) or activated esters. The process is carried out, if necessary, in the presence of suitable condensation agents, for example in the presence of carbodiimides such as dicyclohexylcarbodiimide, when using acids, and, for example, in the presence of basic agents, such as triethylamine or pyridine, when using reactive acid derivatives.

An acyl group can also be introduced stepwise; thus a compound obtainable according to the process can be reacted with a carbonyldihalide, such as phosgene, and the resulting halogen compound, for example chlorocarbonyloxy compound, can be treated with an alcohol, for example 2,2,2-trichloroethanol or 2-bromoethanol, phenacyl alcohol or tert.-butanol, thus a hydroxyl group being acylated stepwise with an etherified hydroxycarbonyl group, for example the 2,2,2-trichloroethoxycarbonyl, 2-bromoethoxycarbonyl, phenacyloxycarbonyl or tert.-butoxycarbonyl group. The acylation reaction can be carried out in the presence or absence of solvents or solvent mixtures, if necessary with cooling or warming, in a closed vessel under pressure and/or in an inert gas atmosphere, for example in a nitrogen atmosphere, and also stepwise if appropriate.

In a resulting compound, an amino protective group $R_1^A$ or $R_1^b$, especially an easily removable acyl group, can be split off in a manner which is in itself known, for example a tert.-butoxycarbonyl group by treatment with trifluoroacetic acid and a 2,2,2-trichloroethoxycarbonyl, 2-iodoethoxycarbonyl or phenacyloxycarbonyl group by treatment with a suitable metal or a metal compound, for example zinc, or a chromium-II compound, such as chromium-II chloride or chromium-II acetate, advantageously in the presence of a hydrogen-releasing agent, preferably aqueous acetic acid, which together with the metal or the metal compound generates nascent hydrogen. It is furthermore possible, in a resulting compound of the formula I, to split off a suitable acyl group $R_1^A$ or $R_1^b$ in a manner which is in itself known, if desired, after protecting functional groups in such a radical, for example by acylation, esterification or silylation, for example, by treatment with a suitable inorganic acid halide, such as phosphorus pentachloride, preferably in the presence of a basic agent, such as pyridine, to form an imide-halide, reaction of the imidehalide with an alcohol, such as a lower alkanol, for example methanol, and splitting of the imino-ether, for example in an aqueous medium, preferably under acid conditions. If the imide-halide intermediate product obtainable according to the above splitting process, instead of being reacted with an alcohol, is reacted with a salt, such as an alkali metal salt of a carboxylic acid, especially of a sterically hindered carboxylic acid, an N,N-diacylamino compound of the formula I, wherein $R_1^A$ and $R_1^b$ represent acyl groups, is obtained.

In a compound of the formula I, wherein both radicals $R_1^A$ and $R_1^b$ represent acyl groups, one of these groups, preferably the less sterically hindered group, can be split off selectively, for example by hydrolysis or aminolysis.

In a compound of the formula I, wherein $R_1^A$ and $R_1^b$ together with the nitrogen atom represent a phthalimido group, this group can be converted into the free amino group, for example by hydrazinolysis, that is to say on treatment of such a compound with hydrazine.

Certain acyl radicals of an acylamino grouping in compounds obtainable according to the invention, especially the 5-amino-5-carboxyvaleryl radical, can also be split off by treatment with a nitrosylating agent, such as nitrosyl chloride, in a carbocyclic arenediazonium salt, such as benzenediazonium chloride, or by treatment with an agent which furnishes positive halogen, such as a N-halogeno-amide or N-halogeno-imide, for example N-bromosuccinimide, preferably in a suitable solvent or solvent mixture, such as formic acid together with a nitro-lower alkane or cyano-lower alkane, treatment of the reaction product with a hydroxylic material, such as water or a lower alkanol, for example methanol, and, if necessary, working-up of the free amino compound according to methods which are in themselves known.

A formyl group $R_1^A$ can also be split off by treatment with an acid agent, for example p-toluenesulphonic acid or hydrochloric acid, a weakly basic agent, for example dilute ammonia, or a decarbonylating agent, for example tris-(triphenylphosphine)-rhodium chloride.

A triarylmethyl group, such as the trityl group $R_1^A$, can, for example, be split off by treatment with an acid agent, such as a mineral acid, for example hydrochloric acid.

In a compound of the formula I, wherein $R_1^a$ and $R_1^b$ represent hydrogen, the free amino group can be acylated according to methods of acylation which are in themselves known, for example by treatment with carboxylic acids or reactive acid derivatives thereof, such as halides, for example fluorides or chlorides, or anhydrides (whereby there are also to be understood the internal anhydrides of carboxylic acids, that is to say ketenes, or of carbamic acids or thiocarbamic acids, that is to say isocyanates or isothiocyanates, or mixed anhydrides, such as those which can, for example, be formed with chloroformic acid lower alkyl esters, such as chloroformic acid ethyl esters, or trichloroacetic acid chloride) or activated esters, or with substituted formimino derivatives, such as substituted N,N-dimethylchloroformimino derivatives, or an N-substituted N,N-diacylamine, such as an N,N-diacylated aniline, reaction being carried out, if necessary in the presence of suitable condensation agents, for example of carbodiimides, such as dicyclohexylcarbodiimide, when using acids, and, for example, of basic agents, such as triethylamine or pyridine, when using reactive acid derivatives, it also being possible, where appropriate, to start from salts, for example ammonium salts of compounds of the formula I, wherein $R_2$ represents hydrogen.

An acyl group can also be introduced if a compound of the formula I, wherein $R_1^a$ and $R_1^b$ represent hydrogen, is reacted with an aldehyde, such as an aliphatic, aromatic or araliphatic aldehyde, the resulting Schiff's base is acylated, for example according to the methods indicated above, and the acylation product is hydrolysed, preferably in a neutral or weakly acid medium.

An acyl group can also be introduced stepwise. Thus, it is for example possible, in a compound of the formula I having a free amino group, to introduce a halogeno-lower alkanoyl group, for example a bromoacetyl group, or to introduce a halogenocarbonyl group, for example a chlorocarbonyl group, for example by treatment with a carbonic acid dihalide, such as phosgene, and to react an N-(halogeno-lower alkanoyl)-amino compound or N-(halogenocarbonyl)-amino compound thus obtainable with suitable exchange reagents, such as basic compounds, for example tetrazole, thio compounds, for example 2-mercapto-1-methyl-imidazole, or metal salts, for example sodium azide, or alcohols, such as lower alkanols, for example tert.-butanol, thus obtaining substituted N-lower alkanoylamino or N-hydroxycarbonylamino compounds. It is furthermore possible, for example, to react a compound of the formula I, wherein $R_1^a$ represents a glycyl group which is preferably substituted in the α-position, such as phenylclycyl, and $R_1^b$ represents hydrogen, with an aldehyde, e.g. formaldehyde, or a ketone, such as a lower alkanone, for example acetone, and thus to obtain compounds of the formula I, wherein $R_1^A$ and $R_1^b$ together with the nitrogen atom represent a 5-oxo-1,3-diazacyclopentyl residue which is preferably substituted in 4-position and optionally substituted in the 2-position.

In both reactants, free functional groups can be transiently protected, in a manner which is in itself known, during the acylation reaction and be liberated after the acylation by means of methods which are in themselves known. Thus, amino or carboxyl groups, for example, present in the acyl residue are preferably protected during the acylation reaction, for example, in the form of acylamino. e.g. 2,2,2-trichloroethoxycarbonylamino, 2-bromoethoxycarbonylamino or tert.-butyloxycarbonylamino group and in the form of an esterified carboxyl, e.g. as a diphenylmethoxy group, respectively, and subsequently, optionally after having converted a protective group, e.g. a 2-bromoethoxycarbonyl into a 2 iodoethoxycarbonyl group, are split, for example, upon treatment with suitable reducing reagents, e.g. zinc in the presence of aqueous acetic acid, or by treatment with trifluoroacetic acid.

The acylation can also take place by replacement of an already existing acyl group by a different, preferably a sterically hindered, acyl group, for example according to the process described above, by manufacturing the imide-halide compound, treating this with a salt of an acid, and hydrolytically splitting off one of the acyl groups present in the product thus obtainable, usually the less sterically hindered acyl group.

In a compound of the formula I, wherein $R_1^a$ and $R_1^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl group and stannyl group. Such groups are introduced in a manner which is in itself known, for example by treatment with a suitable silylating agent, such as a tri-lower alkyl-silyl halide, for example trimethyl-silyl chloride, or an optionally N-mono-lower alkylated, N,N-di-lower alkylated, N-tri-lower alkylsilylated or N-lower alkyl-N-tri-lower alkylsilylated N-(tri-lower alkyl-silyl)-amine (see, for example, British Patent No. 1,073,530) or with a suitable stannylating agent, such as a bis-(tri-lower alkyl-tin)-oxide, for example bis-(tri-n-butyl-tin)-oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound, or a tri-lower alkyl-tin halide, for example tri-n-butyl-tin chloride (see, for example, Netherlands Published Specification 67/17,107).

Salts of compounds of the formula I can be manufactured in a manner which is in itself known, acid addition salts of compounds with basic groups, for example, by treatment with an acid or with a suitable anion exchange reagent. Salts can be converted into the free compounds in the usual manner, acid addition salts, for example, by treatment with a suitable basic agent.

Resulting mixtures of isomers can be separated into the individual isomers according to methods which are in themselves known, for example by fractional crystallisation, adsorption chromatography (column chromatography or thin layer chromatography) or other suitable separation processes. Resulting racemates can be separated into the antipodes in the usual manner, optionally after the temporary introduction of salt-forming groupings, for example by forming a mixture of diastereoisomeric salts with optically active salt-forming agents, separating the mixture into the diastereoisomeric salts and converting the separated salts into the free compounds, or by fractional crystallisation from optically active solvents.

The process also includes those embodiments according to which compounds arising as intermediate products are used as starting substances and the remaining process steps are carried out with these, or the process is stopped at any stage; furthermore, starting substances can be used in the form of derivatives or formed during the reaction.

Preferably, those starting substances are used, and the reaction conditions are so chosen, that the compounds listed initially as being particularly preferred are obtained.

The starting substances of the formula II used according to the process are obtained if a compound of the formula

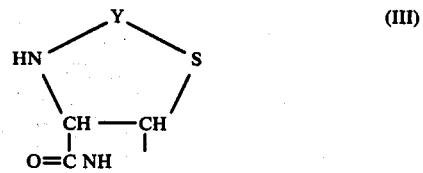

wherein Y represents an optionally substituted methylene group, is oxidised, and in a resulting compound of the formula

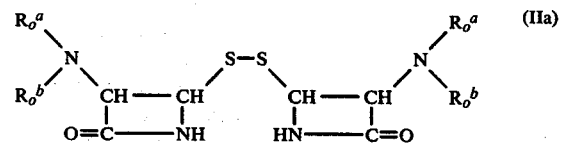

wherein $R_o^a$ and $R_o^b$ represent hydrogen or together represent an optionally substituted methylene group, a protective group $R_1^A$ and/or $R_1^b$ is introduced into the amino group, if desired after splitting off the optionally substituted methylene group referred to above.

In a compound of the formula III, Y preferably represents a monosubstituted or disubstituted methylene group, wherein substituents are preferably optionally substituted monovalent or divalent hydrocarbon radicals, above all appropriate aliphatic hydrocarbon radicals, such as lower alkyl groups, for example methyl, ethyl, n-propyl, isopropyl, n-butyl or isobutyl groups, also lower alkylene groups, for example 1,4-butylene or 1,5-pentylene groups, as well as appropriate cycloaliphatic, cycloaliphatic-aliphatic, aromatic or araliphatic hydrocarbon radicals, such as cycloalkyl groups, for example cyclopentyl or cyclohexyl groups, phenyl groups or phenyl-lower alkyl groups, for example benzyl or phenylethyl groups. Above all, Y represents the isopropylidene or the isobutylidene group, that is to say a methylene radical substituted by two methyl groups or by an isopropyl group.

Oxidising agents used according to the process are above all those which are used for forming disulphide compounds under conditions under which the β-lactam ring is not affected. These are especially halogen, such as bromine and above all iodine, which are advantageously used in the presence of organic solvents, for example optionally substituted hydrocarbons, such as aromatic hydrocarbons, for example benzene, ethers, such as cyclic ethers, for example tetrahydrofurane or dioxane, alcohols, such as lower alkanols, for example methanol or ethanol, or carboxylic acids, such as lower alkane-carboxylic acids, for example acetic acid, or solvent mixtures, and optionally in the presence of water, with cooling (for example temperatures down to about −30° C.), at room temperature or with slight warming, and also, if necessary, under an inert gas atmosphere, such as a nitrogen atmosphere.

Further oxidising agents which are suitable for the oxidation of starting substances are oxidising heavy metal carboxylates, for example lead-IV carboxylates, such as lead-IV alkanoates, especially lower alkanoates, and above all lead tetraacetate, and also lead tetrapropionate or lead tetrastearate and optionally substituted lead tetrabenzoates, for example lead tetrabenzoate or lead tetra-3-bromobenzoate, as well as thallium-III carboxylates, for example thallium-III acetate, or mercury-II carboxylates, such as mercury-II acetate, and these oxidising agents can, if desired, be formed in situ, for example by reaction of lead dioxide or mercury II oxide with an organic carboxylic acid, such as acetic acid.

Advantageously, the above heavy metal carboxylates, especially the corresponding lead-IV compounds, are used in the presence of a source of light, ultraviolet light, as well as light of longer wavelengths, such as visible light, being employed preferentially, optionally with the addition of suitable sensitisers. The UV light preferably has a main wavelength range of above 280 m$\mu$, above all of about 300 m$\mu$ to about 350 m$\mu$; this can be achieved, for example, by suitable filtration of the ultraviolet light through an appropriate filter, for example a pyrex filter, or through suitable solutions, such as salt solutions, or other liquids which absorb light of shorter wavelengths, such as benzene or toluene. The ultraviolet light is preferably generated by means of a high pressure mercury vapour lamp.

The oxidation with a heavy metal carboxylate oxidising agent is usually carried out in the presence of a suitable diluent, such as benzene, acetonitrile or acetic acid, if necessary with cooling or with warming and/or in an inert gas atmosphere.

Further oxidising agents which can be used in the above reaction are oxygen (for example as pure oxygen or in the form of air) in the presence of a heavy metal salt used as the catalyst, for example a cupric salt or ferric salt, such as ferric chloride or ferric sulphate, and preferably in the presence of a solvent, such as acetic acid, hypohalite compounds, especially alkali metal hypohalites, for example sodium hypoiodite, as well as organic hypohalites, such as tert.-butyl hypochlorite, suitable ferric salts and ferric complexes, such as ferric chloride, preferably in the presence of an organic solvent, for example ether, acetic acid or ethanol, and optionally in the presence of water, or potassium ferricyanide, 1,2-diiodoethane in the presence of an organic solvent, for example acetone, tetrahydrofurane or ethanol, or thiocyanogen in the presence of a suitable organic solvent, for example acetic acid.

In a disulphide compound of the formula IIa obtainable according to the process, in which the radicals $R_o{}^a$ and $R_o{}^b$ together represent an optionally substituted methylene group, such a group can be hydrolytically replaced by hydrogen; this splitting-off can already occur during the oxidation reaction if the latter is carried out in the presence of water.

In a disulphide compound of the formula IIa obtainable according to the process, in which the amino groups are unsubstituted or contain an optionally substituted methylene radical as a substituent, these groups can be protected, for example acylated, according to methods which are in themselves known, for example as described above. In doing so, an optionally substituted methylene radical, possibly in a modified form, which is formed by the groups $R_o{}^a$ and $R_o{}^b$, can be split off.

The intermediate products of the formula III required for the manufacture of the starting substances, wherein Y represents a disubstituted methylene group, are known (see, for example, Austrian Patent No. 264,533) or can be manufactured according to the processes used for the known compounds. Compounds wherein Y denotes an unsubstituted or monosubstituted methylene group can, for example, be obtained if a compound of the formula III, wherein Y represents a disubstituted methylene group, is reacted with an aldehyde or with a reactive derivative, such as a hydrate or a reactive polymeric product of such an aldehyde. This reaction is usually carried out in a solvent, such as an organic solvent which is miscible with water, such as an alcohol or ether which is miscible with water, for example dioxane, or in a suitable mixture of solvents. Preferably, water is added and the process carried out in the presence of an acid agent, such as an inorganic or organic acid, for exmple an organic carboxylic acid or preferably an organic sulphonic acid, such as p-toluenesulphonic acid, if desired or required, with cooling or preferably with warming and/or in a closed vessel and/or in an inert gas atmosphere, for example under nitrogen.

The compound of the formula III, wherein Y represents a methylene radical substituted by the isopropyl group, can be manufactured from easily accessible starting substances if a penam-3-carboxylic acid compound IVa of the formula

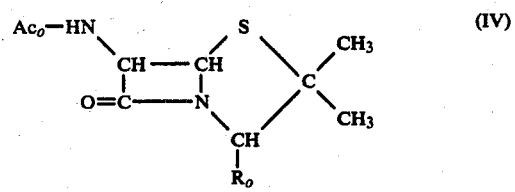

in which $Ac_o$ represents the acyl radical of an organic carboxylic acid, and wherein free functional groups which may be present, such as hydroxyl or mercapto groups, and especially amino and carboxyl groups, are optionally protected, for example by acyl groups or in the form of ester groups, and $R_o$ represents a carboxyl group —C(=O)—OH (compound IVa) or a salt thereof is converted into the corresponding acid azide compound of the formula IV, wherein $R_o$ represents the azido-carbonyl radical —C(=O)—N$_3$ (compound IVb), the latter is converted, with elimination of nitrogen, into the corresponding isocyanate compound of the formula IV, wherein $R_o$ denotes the isocyanato group —N=C=O (compound IVc), and this is simultaneously or subsequently treated with a compound of the formula H—X$_2$ (V), wherein X$_2$ is an etherified hydroxy group, which together with the carbonyl portion in the isocyanato grouping forms an esterified carboxyl group which can be split under neutral or acid conditions, and in a resulting compound of the formula IV, wherein $R_o$ represents the radical of the formula —NH—C(=O)—X$_2$ (compound IVd), the acyl radical $Ac_o$ is replaced by hydrogen and, if desired, the latter is replaced by an acyl group which can be split off in the following step. In the penam compound thus obtainable, of the formula

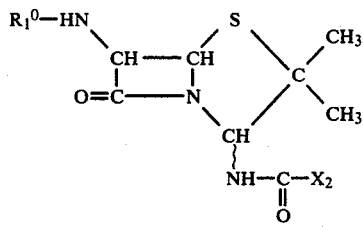

(VI)

wherein $R_1^o$ represents hydrogen or an acyl group $Ac^o$ which can be split off under the reaction conditions of the subsequent process step, the group of the formula —C(=O)—X$_2$ is split under neutral or weakly acid conditions, with simultaneous or subsequent treatment with water, and the 4,4-dimethyl-5-thia-2,7-diazabicyclo[4.2.0]oct-2-en-8-one which may be formed is isolated, or the carbon-nitrogen double bond therein is reduced.

An acyl group $Ac_o$ occurring in the compounds of the formula IV can represent any acyl radical of an organic carboxylic acid having optionally protected functional groups, above all an acyl radical contained in fermentatively or biosynthetically preparable N-acyl derivatives of 6-amino-penam-3-carboxylic acid compounds, such as a monocyclic arylacetyl or aryloxyacetyl radical and also an optionally substituted lower alkanoyl or lower alkenoyl radical, for example the 4-hydroxy-phenylacetyl, hexanoyl, octanoyl, 3-hexenoyl, 5-amino-5-carboxy-valeroyl, n-butylthioacetyl or allylthioacetyl radical especially the phenylacetyl or phenyloxyacetyl radical, or an acyl radical which can preferably be split off easily under acid conditions, such as the acyl radical of a half-ester of carbonic acid, for example the tert.-butoxycarbonyl radical.

The conversion of an acid compound IVa or of a suitable salt, especially of an ammonium salt, into the corresponding acid azide IVb can, for example, be effected by conversion into a mixed anhydride (for example by treatment with a halogenoformic acid lower alkyl esters, such as chloroformic acid ethyl ester, in the presence of a basic agent, such as triethylamine) and treatment of such an anhydride with an alkali metal azide, such as sodium azide. The acid azide compound IVb thus obtainable can be converted into the desired isocyanate compound IVc under the reaction conditions, for example on warming, in the absence or presence of a compound of the formula V, and the compound IVc usually does not have to be isolated and can be converted directly, in the presence of a compound of the formula V, into the desired compound of the formula VI.

Etherified hydroxyl groups $X_2$ which together with the carbonyl grouping form an esterified carboxyl group which can be split under neutral or weakly acid conditions, are especially the groups of the formula —O—$R_o^a$, —O—$R_o^b$ and —O—$R_o^c$, wherein $R_o^a$, $R_o^b$ and $R_o^c$ correspond to the abovementioned radicals $R_2^a$, $R_2^b$ and $R_2^c$.

The reaction of a compound of the formula IVc with a compound of the formula V, especially with a 2-halogenoethanol $R_o^a$—OH, for example with 2,2,2-trichloroethanol or 2-bromoethanol, an arylcarbonylmethanol $R_o^b$—OH, for example phenacylalcohol, or an arylmethanol $R_o^c$—OH, for example 4,5-dimethoxy-2-nitro-benzyl alcohol, is optionally carried out in an inert solvent, for example in a halogenated hydrocarbon, such as carbon tetrachloride, chloroform or methylene chloride, or in an aromatic solvent, such as benzene, toluene or chlorobenzene, preferably with warming.

The acylamino group $Ac_o$—HN— can be split according to processes which are in themselves known, for example by treatment of a compound with an imide-halide-forming agent, reaction of the resulting imide-halide with an alcohol and cleavage of the resulting imino-ether, whereby a carboxyl group which is protected, for example by an organic silyl radical, may already be liberated in the course of the reaction, for example on treatment with an alcohol.

Imide-halide-forming agents in which halogen is bonded to an electrophilic central atom are above all acid halides, such as acid bromides and especially acid chlorides. These are above all acid halides of inorganic acids, above all of phosphorus-containing acids, such as phosphorus oxyhalides, phosphorus trihalides and especially phosphorus pentahalides, for example phosphorus oxychloride, phosphorus trichloride and above all phosphorus pentachloride, and also pyrocatechylphosphorus trichloride, as well as acid halides, especially acid chlorides, of acids containing sulphur or of carboxylic acids, such as thionyl chloride, phosgene or oxalyl chloride.

The reaction with one of the imide-halide-forming agents mentioned is preferably carried out in the presence of a suitable base, especially an organic base, above all a tertiary amine, for example a tertiary aliphatic monoamine or diamine, such as a tri-lower alkylamine, for example trimethylamine, triethylamine or ethyldiisopropylamine, or of an N,N,N',N'-tetra-lower alkyl-lower alkylenediamine, for example N,N,N',N'-tetramethyl-1,5-pentylenediamine or N,N,N',N'-tetramethyl-1,6-hexylenediamine, a monocyclic or bicyclic monoamine or diamine, such as an N-substituted, for example N-lower alkylated, alkyleneamine, azaalkyleneamine or oxaalkyleneamine, for example N-methyl-piperidine or N-methylmorpholine, also 2,3,4,6,7,8-hexahydro-pyrrolo[1,2-a]pyrimidine (diazabicyclononene; DBN) or a tertiary aromatic amine, such as a di-lower alkylaniline, for example N,N-dimethylaniline, or above all a tertiary heterocyclic, monocyclic or bicyclic base, such as quinoline or isoquinoline, but especially pyridine, preferably in the presence of a solvent, such as an optionally halogenated, for example chlorinated, aliphatic or aromatic hydrocarbon, for example methylene chloride. Approximately equimolar amounts of the imide-halide-forming agent and of the base can be used; the latter can, however, also be present in excess or in a less than equivalent amount, for example in about 0.2-fold to about 1-fold amount or in up to about a 10-fold excess, especially in about 3-5-fold excess.

The reaction with the imide-halide-forming agent is preferably carried out with cooling, for example at temperatures of about −50° C. to about +10° C., but higher temperatures, that is to say, for example, up to about 75° C., can also be used if the stability of the starting substances and products permits an elevated temperature.

The imide-halide product, which is usually further processed without isolation, is reacted according to the process with an alcohol, preferably in the presence of one of the above-mentioned bases, to give the imino-ether. Suitable alcohols are, for example, aliphatic and araliphatic alcohols, above all optionally substituted, such as halogenated, for example chlorinated lower alkanols, or lower alkanols possessing additional hydroxyl groups, for example ethanol, n-propanol, isopropanol or n-butanol, especially methanol, and also 2,2,2-trichloroethanol, as well as optionally substituted phenyl-lower alkanols, such as benzyl alcohol. Usually, an excess, for example up to an about 100-fold excess, of the alcohol is used, and the process is preferably carried out with cooling, for example at temperatures of about −50° C. to about 10° C.

The imino-ether product can advantageously be split without isolation. The splitting of the imino-ether can be achieved by treatment with a suitable hydroxy compound. For this, water is preferably used, or an aqueous mixture of an organic solvent, such as of an alcohol, especially of a lower alkanol, for example methanol. The reaction is usually carried out in an acid medium, for example at a pH value of about 1 to about 5, which can, if necessary, be established by adding a basic agent, such as an aqueous alkali metal hydroxide, for example sodium hydroxide or potassium hydroxide, or an acid, for example a mineral acid or organic acid, such as hydrochloric acid, sulphuric acid, phosphoric acid, fluoboric acid, trifluoroacetic acid or p-toluenesulphonic acid.

The three-stage process, described above, for splitting off an acyl group is advantageously carried out without isolation of the imide-halide and imino-ether intermediate products, usually in the presence of an organic solvent which is inert towards the reactants, such as an optionally halogenated hydrocarbon, for example methylene chloride, and/or in an inert gas atmosphere, such as a nitrogen atmosphere.

An acyl group $Ac^o$ which can be split off under the reaction conditions of the conversion of a compound of the formula VI into a compound of the formula III, wherein Y represents a 1-isobutylidene group, is, for example, a group of the formula $-C(=O)-X_2$, wherein $X_2$ has the abovementioned meaning, especially a group of the formula $-C(=O)-O-R_o^a$, $-C(=O)-O-R_o^b$ or $-C(=O)-O-R_o^c$, wherein $R_o^a$, $R_o^b$ and $R_o^c$ have the abovementioned meanings, but can also represent any other acyl group which can be split off under the reaction conditions mentioned, especially a grouping which can be split off under acid conditions.

Such an acyl group can be introduced in a manner which is in itself known, for example as described above.

The splitting of the group $-C(=O)-X_2$ in an intermediate product of the formula VI depends on the nature of this group, the splitting either being carried out in the presence of at least one mol, and normally an excess, of water, or the reaction product being subsequently treated with water.

The splitting of an esterified carboxyl group of the formula $-C(=O)-X_2$, which in a compound of the formula VI can also represent the radical $Ac^o$, and wherein $X_2$ represents the group $-O-R_o^a$ or $-O-R_o^b$, is effected by treatment with a chemical reducing agent in the presence of an at least equimolar amount of water, usually in the presence of an excess of water. The reaction is carried out under mild conditions, in most cases at room temperature or even with cooling.

Chemical reducing agents are the reducing agents of this nature which has been mentioned in the process according to the invention described above, such as reducing metals, metal alloys or metal compounds, preferably in the presence of hydrogen-releasing agents, above all zinc in the presence of aqueous acetic acid.

In a compound of the formula VI wherein $X_2$ represents a radical of the formula $-O-R_o^c$, the group of the formula $-C(=O)-X_2$, which can also represent the group $Ac^o$, can be split by irradiation with light, preferably with ultraviolet light. Herein light of longer or shorter wavelengths is used depending on the nature of the substituent $R_o^c$. Thus, for example, groups of the formula $-C(=O)-O-R_o^c$, wherein $R_o^c$ represents an arylmethyl radical, especially a benzyl radical, which is substituted by a nitro group in the 2-position of the aryl radical and optionally contains further substituents, such as lower alkoxy groups, for example methoxy groups, for example the 4,5-dimethoxy-2-nitro-benzyl radical, are split by irradiation with ultraviolet light with a wavelength range of above 290 mμ, whilst those in which $R_o^c$ represents an arylmethyl radical, for example benzyl radical, which is optionally substituted in the 3-, 4- and/or 5-position, for example by lower alkoxy and/or nitro groups, are split by irradiation with ultraviolet light having a wavelength range of below 290 mμ. In the former case, the process is carried out with a high pressure mercury vapour lamp, preferably using pyrex glass as the filter, for example at a main wavelength range of about 315 mμ, and in the latter case it is carried out with a lower pressure mercury vapour lamp, for example at a main wavelength range of about 254 mμ.

The irradiation reaction is carried out in the presence of a suitable polar or non-polar organic solvent or of a mixture; solvents are, for example, optionally halogenated hydrocarbons, such as optionally chlorinated lower alkanes, for example methylene chloride, or optionally chlorinated benzenes, for example benzene, as well as alcohols, such as lower alkanols, for example methanol, or ketones, such as lower alkanones, for example acetone. The reaction is preferably carried out at room temperature or, if necessary, with cooling, usually in an inert gas atmosphere, for example in a nitrogen atmosphere. It is preferably carried out in the presence of water; it is, however, also possible to treat the irradiation product subsequently with water, for example by working up the product obtained in the presence of water.

The 4,4-dimethyl-5-thia-2,7-diazabicyclo[4.2.0]oct-2-en-8-one which may be formed as an intermediate product, and which in particular arises in the case of the non-reductive splitting of a group of the formula $-C(=O)-X_2$ in a compound of the formula VI, wherein $X_2$ represents the group of the formula $-O-R_o^c$, and also arises on splitting a group of the formula $-C(=O)-X_2$ in a compound of the formula VI, wherein $X_2$ represents the group of the formula $-O-R_o^a$, by means of a strongly reducing metal salt, can be converted by exhaustive reduction into the desired 3-isopropyl-4-thia-2,6-diazabicyclo[3.2.0]heptan-7-one, or can be isolated from a mixture with the latter. Preferably, chemical reducing agents are used for the reduction of the carbon-nitrogen double bond in the 4,4-dimethyl-5-thia-2,7-diazabicyclo[4.2.0]oct-2-en-8-one, which takes place with simultaneous rearrangement to 3-isopropyl-4-thia-2,6-diazabicyclo [3.2.0]heptan-7-one, above all reducing metals or metal compounds, such as those mentioned above, preferably in the presence of hydrogen-releasing agents, especially zinc in the presence of an acid, such as acetic acid, or in the presence of an alcohol.

A mixture of 3-isopropyl-4-thia-2,6-diazabicyclo[3.2.0]heptan-7-one and of 4,4-dimethyl-5-thia-2,7- diazabicyclo[4.2.0]oct-2-en-8-one, such as is above all produced on reductive splitting of the group of the formula —C(=O)—X$_2$ in a starting material of the formula VI, wherein X$_2$ denotes a group of the formula —O—R$_o^a$ or —O—R$_o^b$, can be separated into the individual compounds according to methods of separation which are in themselves known, for example by fractional crystallisation, adsorption chromatography (column chromatography or thin layer chromatography) or other suitable processes of separation.

In the manufacture of compounds of the formula VI, intermediate products can, at suitable stages, be converted into one another. Thus it is for example possible to replace an aliphatically bonded chlorine atom and especially a bromine atom in the radical X$_2$, such as the 2-bromoethoxy radical, by an iodine atom, for example by treatment with a suitable iodide salt, such as an alkali metal iodide, for example potassium iodide, in a suitable solvent, such as acetone, for example to convert the 2-bromoethyl radical into the 2-iodoethyl radical.

As mentioned, the compounds of the formula I represent valuable intermediate products, which are in particular suitable for the manufacture of pharmacologically valuable compounds, for example of the type of 7β-amino-ceph-3-em-4-carboxylic acid and N-acyl derivatives thereof, the latter in particular being active against micro-organisms, such as Gram-positive and Gram-negative bacteria.

Thus, it is possible to react a compound of the formula I, wherein R$_3$ and R$_4$ have the above given meaning, but wherein R$_3$ represents above all hydrogen, R$_1^a$ denotes an amino protective group R$_1^A$, R$_1^b$ has the abovementioned meaning and the radical R$_2$ represents the acyl radical of the formula —C(=O)—X$_1$, with a compound of the formula

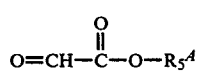
(VII)

wherein R$_5^A$ represents an organic radical which together with the —C(=O)—O— grouping forms a protected carboxyl group, or with a reactive derivative thereof, and to convert the secondary hydroxyl group in the addition compound of the formula

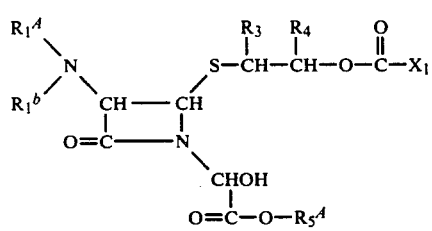
(VIII)

into a reactive esterified hydroxyl group. The reactive ester of the formula

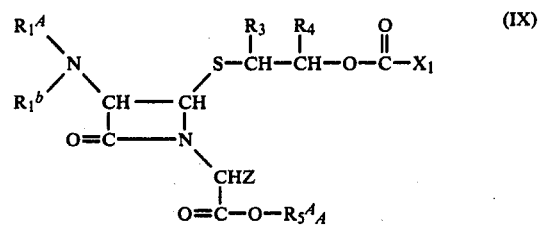
(IX)

wherein Z represents a reactive esterified hydroxyl group, above all a halogen atom, especially a chlorine or bromine atom, or an organic sulphonyloxy group, for example a 4-methylphenylsulphonyloxy or methylsulphonyloxy group, is reacted with a phosphine compound of the formula

(X)

wherein each of the radicals R$_a$, R$_b$ and R$_c$ represent an optionally substituted hydrocarbon radical, and thus, if necessary after splitting off the elements of an acid of the formula H—Z (XIa) from a phosphonium salt compound of the formula

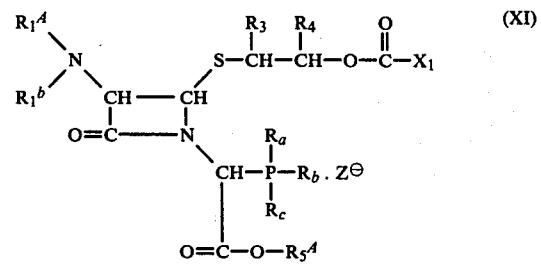
(XI)

obtainable as an intermediate product, the phosphoranylidene compound of the formula

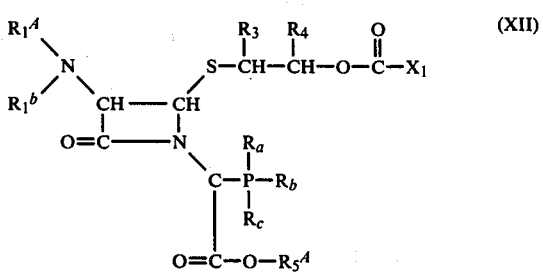
(XII)

is obtained, in which the esterified carboxyl grouping —C(=O)—X$_1$ is split. In a resulting compound of the formula

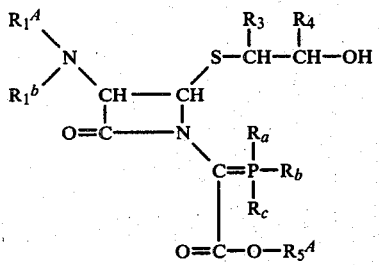

(XIII)

in which $R_3$ represents hydrogen, the hydroxyl group is oxidised to the oxo group. In a ceph-3-em-compound of the formula

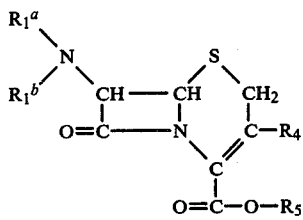

(XIV)

thus obtainable, in which $R_1{}^a$ represents an amino protective group $R_1{}^A$, $R_1{}^b$ has the above meaning and $R_5$ represents the organic radical $R_5{}^A$, and which is produced by cyclisation from a carbonyl compound of the formula

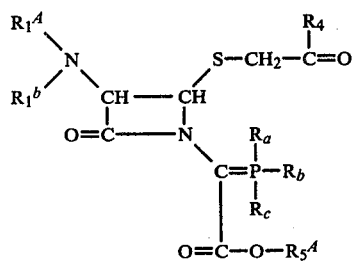

(XIVa)

which is formed under the reaction conditions but need not be isolated, it is possible, if desired, to split off an amino protective group $R_1{}^A$ and/or $R_1{}^b$ optionally to protect the free amino group in a compound thus obtainable and/or, if desired, to convert a protected carboxyl group of the formula —C(=O)—O—$R_5{}^A$ into the free carboxyl group or into a different protected carboxyl group of the formula —C(=O)—O—$R_5{}^A$ and optionally to convert a free carboxyl group into a protected carboxyl group of the formula —C(=O)—O—$R_5{}^A$ and/or, if desired, to convert a resulting compound having a salt-forming group into a salt or a resulting salt into the free compound or into a different salt and/or, if desired, to separate a resulting isomer mixture into the individual isomers.

In a compound of the formula I to be used as the starting substance, the radical $R_2$ denotes the acyl radical of the formula —C(=O)—$X_1$, the acylated hydroxyl group in particular represents a group of the formula —O—C(=O)—O—$R_o{}^a$, —O—C(=O)—O—$R_o{}^b$, —O—C(=O)—O—$R_o{}^c$, —O—C(=O)—O—$R_o{}^d$, —O—C(=O)—O—$R_o{}^e$ or —O—C(=O)—O—$R_o{}^f$, wherein $R_o{}^a$, $R_o{}^b$, $R_o{}^c$, $R_o{}^d$, $R_o{}^e$ and $R_o{}^f$ have the abovementioned meanings and above all represent 2,2,2-trichloroethyl, phenacyl, 4,5-dimethoxy-2-nitro-benzyl or tert.-butyl radicals.

In a glyoxylic acid compound of the formula VII the radical $R_5{}^A$ above all represents a group $R_o{}^a$, $R_o{}^b$, $R_o{}^c$, $R_o{}^d$, $R_o{}^e$ and $R_o{}^f$.

The addition of the glyxoylic acid ester compound of the formula VII to the nitrogen atom of the lactam ring of a compound of the formula I preferably takes place at elevated temperature, above all at about 50° C. to about 150° C., and in particular in the absence of a condensation agent and/or without the formation of a salt. Instead of the free glyoxylic acid ester compound a reactive oxo derivative thereof, above all a hydrate, can also be used, and when using the hydrate the water produced can, if necessary, be removed by distillation, for example azeotropically.

The reaction is preferably carried out in the presence of a suitable solvent such as, for example, dioxane or toluene, or solvent mixture, in a closed vessel under pressure and/or in the atmosphere of an inert gas, such as nitrogen, if desired or required.

In a compound of the formula VIII the secondary hydroxyl group can be converted in a manner which is in itself known into a reactive hydroxyl group esterified by a strong acid, especially into a halogen atom or an organic sulphonyloxy group. For this suitable halogenating agents are, for example, used, such as a thionyl halide, for example thionyl chloride, a phosphorus oxyhalide, especially phosphorus oxychloride, or a halogenophosphonium halide, such as triphenylphosphonium dibromide or triphenylphosphonium diiodide, or a suitable organic sulphonic acid halide, such as a sulphonic acid chloride, the reaction preferably being carried out in the presence of a basic agent, above all an organic basic agent, such as an aliphatic tertiary amine, for example triethylamine or diisopropylethylamine, or of a heterocyclic base of the pyridine type, for example pyridine or collidine. Preferably, the reaction is carried out in the presence of a suitable solvent, for example dioxane or tetrahydrofurane, or of a solvent mixture, if necessary with cooling and/or in the atmosphere of an inert gas, such as nitrogen.

In a resulting compound of the formula IX, a reactive esterified hydroxyl group Z can be converted in a manner which is in itself known into another reactive esterified hydroxyl group. Thus it is for example possible to replace a chlorine atom by a bromine atom or iodine atom by treating the appropriate chlorine compound with a suitable bromine or iodine reagent, especially with an inorganic bromide or iodide salt, such as lithium bromide, preferably in the presence of a suitable solvent, such as ether.

In a compound of the formula X each of the groups $R_a$, $R_b$ and $R_c$ above all denotes a lower alkyl radical which is optionally substituted, for example by etherified or esterified hydroxyl groups, such as lower alkoxy groups or halogen atoms, or a phenyl radical which is optionally substituted, for example by aliphatic hydrocarbon radicals, such as lower alkyl groups, or etherified or esterified hydroxyl groups, such as lower alkoxy groups or halogen atoms, or nitro groups.

The reaction of a compound of the formula IX with the phosphine compound of the formula X, wherein each of the groups $R_a$, $R_b$ and $R_c$ above all represents phenyl or a lower alkyl radical, especially the n-butyl radical, is preferably carried out in the presence of a suitable inert solvent, such as an aliphatic, cycloaliphatic or aromatic hydrocarbon, for example hexane, cyclohexane, benzene or toluene, or of an ether, for example dioxane, tetrahydrofurane or diethylene glycol dimethyl ether, or of a solvent mixture. If necessary, the process is carried out with cooling or at elevated temperature and/or in the atmosphere of an inert gas, such as nitrogen.

A phosphonium salt compound of the formula XI formed as an intermediate usually spontaneously loses the elements of the acid of the formula H-Z (XIa); if necessary, the phosphonium salt compound can be decomposed by treatment with a weak base, such as an organic base, for example diisopropylethylamine or pyridine, and converted into the phosphoranylidene compound of the formula XII.

The splitting of the esterified carboxyl group of the formula $-C(=O)-X_1$ in a compound of the formula XII can be carried out in various ways, depending on the nature of the group $X_1$. Thus it is possible to split a grouping $-C(=O)-X_1$, wherein $X_1$ represents the group of the formula $-O-R_o{}^a$ or $-O-R_b{}^b$, by treatment with a chemical reducing agent, for example one of the abovementioned reducing agents, such as zinc, which is advantageously used in the presence of an acid or of an alcohol, optionally with the addition of water, for example in the presence of aqueous acetic acid, and to split a grouping of the formula $-C(=O)-X_1$, wherein $X_1$ represents the group of the formula $-O-R_o{}^c$, by irradiation with light, especially with ultraviolet light; these splitting reactions can be carried out according to the processes described above.

An esterified carboxyl grouping of the formula $-C(=O)-O-R_o{}^d$ or $-C(=O)-O-R_o{}^e$ can be split by treatment with an acid agent, especially with an acid, such as a strong organic carboxylic acid, for example an optionally substituted lower alkanecarboxylic acid which preferably contains halogen atoms, such as acetic acid or trifluoroacetic acid, or with formic acid or a strong organic sulphonic acid, for example p-toluenesulphonic acid. Usually an excess of an acid reagent which is liquid under the reaction conditions is used as the diluent and the reaction is carried out at room temperature or with cooling, for example to between about $-20°$ C. and about $+10°$ C.

An esterified carboxyl grouping $-C(=O)-O-R_o{}^f$ can be split hydrolytically under neutral or weakly acid or basic conditions, for example at a pH value of about 4 to about 9, for example by treatment with water, a weakly acid agent, such as a weak acid or a weakly acid buffer solution, or a weakly basic agent, such as an alkali metal bicarbonate, such as sodium bicarbonate, or a suitable buffer (pH about 7 to about 9) such as dipotassium hydrogen phosphate buffer, in the presence of water and preferably of an organic solvent, such as methanol or acetone.

At the same time, the esterified carboxyl groups of the formulae $-C(=O)-X_1$ and $-C(=O)-O-R_5{}^A$ in a compound of the formula XII preferably differ from one another in such a way that under the conditions of splitting of the esterified carboxyl group of the formula $-C(=O)-X_1$ the esterified carboxyl group of the formula $-C(=O)-O-R_5{}^A$ remains intact. If, for example, the esterified carboxyl group of the formula $-C(=O)-X_1$ represents an esterified carboxyl group which can be split on treatment with a chemical reducing agent, such as zinc in the presence of aqueous acetic acid, for example a grouping of the formula $-C(=O)-O-R_o{}^a$ or $-C(=O)-O-R_o{}^b$, wherein $R_o{}^a$ preferably represents the 2,2,2-trichloroethyl and $R_o{}^b$ above all represents the phenacyl group, the esterified carboxyl group of the formula $-C(=O)-O-R_5{}^A$ for example represents an esterified carboxyl group $-C(=O)-O-R_5{}^A$ which can be split on treatment with a suitable acid, such as trifluoroacetic acid, for example a grouping of the formula $-C(=O)-O-R_o{}^d$, wherein $R_o{}^d$ preferably represents the tert.-butyl group.

The oxidation of a compound of the formula XIII can surprisingly be carried out by treatment with an oxidising organic sulphoxide compound in the presence of agents possessing dehydrating or water-absorbing properties. Possible oxidising sulphoxide compounds are above all aliphatic sulphoxide compounds, such as di-lower alkylsulphoxides, above all dimethylsulphoxide, or lower alkylenesulphoxides, for example tetramethylenesulphoxide. As agents with dehydrating or water-absorbing properties there should above all be mentioned acid anhydrides, especialy anhydrides of organic carboxylic acids, such as of aliphatic or aromatic carboxylic acids, for example anhydrides of lower alkanecarboxylic acids, especially acetic anhydride as well as propionic anhydride or benzoic anhydride, and also anhydrides of inorganic acids, especially of phosphoric acids, such as phosphorus pentoxide. The above anhydrides, above all of organic carboxylic acids, for example acetic anhydride, are preferably used in an approximately 1:1 mixture with the sulphoxide oxidising agent. Further dehydrating or water-absorbing agents are carbodiimides, above all dicyclohexylcarbodiimide, and also diisopropylcarbodiimide, or ketenimines, for example diphenyl-N-p-tolylketenimine; these reagents are preferably used in the presence of acid catalysts, such as phosphoric acid or pyridinium trifluoroacetate or pyridinium phosphate. Sulphur trioxide can also be used as a dehydrating or water-absorbing agent, normally being employed in the form of a complex, for example with pyridine.

Usually, the sulphoxide oxidising agent is used in excess. Sulphoxide compounds which are liquid under the reaction conditions, especially dimethylsulphoxide, can for example simultaneously serve as solvents; additionally, inert diluents, such as benzene, or mixtures of solvents, can be employed as solvents.

The above oxidation reaction is carried out with cooling if desired, but in most cases at room temperature or slightly elevated temperature. An aldehyde compound of the formula XIVa obtainable as an intermediate product according to the process is directly cyclised under the reaction conditions, and without being isolated, to give the 7β-amino-ceph-3-em-4-carboxylic acid compound of the formula XIV. In the case that $R_4$ is other than hydrogen the keto compounds of formula XIVa can be isolated and/or be converted into the ceph-3-em compounds of formula XIV at elevated temperatures, for example at about 50° C. to about 150° C., e.g. as described in Belgian Patent No. 791,159.

In a resulting compound of the formula XI, wherein $R_1{}^b$ is primarily hydrogen an amino protective group $R_1{}^A$, especially an easily removable acyl group, can be split off in a manner which is in itself known, a tert.-butoxycarbonyl group, for example, by treatment with trifluoroacetic acid and a 2,2,2-trichloroethoxycarbonyl group by treatment with a suitable metal or a metal compound, for example tin, or a chromium-II compound, such as chromium-II chloride or chromium-II acetate, advantageously in the presence of a hydrogen-releasing agent which together with the metal or the metal compound generates nascent hydrogen, preferably in the presence of aqueous acetic acid. It is furthermore possible, in a resulting compound of the formula XIV, wherein a carboxyl group —C(=O)—O—$R_5$ preferably represents a carboxyl group which is protected, for example by esterification, including by silylation or stannylation, for example with a suitable organic halogenosilicon compound or halogen-tin-IV compound, such as trimethylchlorosilane, to split off a suitable acyl group $R_1^4$, wherein free functional groups which may be present are preferably protected, by treatment with an imide-halide-forming agent, such as a suitable inorganic acid halide, for example phosphorus pentachloride, preferably in the presence of a basic agent, such as pyridine, reaction of the resulting imide-halide with an alcohol, such as a lower alkanol, for example methanol, and splitting of the resulting imino-ether in an aqueous or alcoholic medium, preferably under acid conditions. A triarylmethyl group $R_1^A$ can, for example, be split off as described above.

In a compound of the formula XIV, wherein $R_1^a$ and $R_1^b$ denote hydrogen, the free amino group can be protected, in particular acylated, according to substitution processes which are in themselves known, for example as described above.

In a compound of the formula XIV having an esterified carboxyl group, with the latter representing, for example, a carboxyl group of the formula —C(=O)—O—$R_5^A$ which can easily be converted into the free carboxyl group, this esterified carboxyl group can be converted into the free carboxyl group in a manner which is in itself known, for example in accordance with the nature of the esterifying radical $R_5^A$, a grouping of the formula —C(=O)—O—$R_o^a$ or —C(=O)—O—$R_o^b$ for example by treatment with a chemical reducing agent, such as a metal, for example zinc, or a reducing metal salt, such as a chromium-II salt, for example chromium-II chloride, usually in the presence of a hydrogen-releasing agent which together with the metal is able to generate nascent hydrogen, such as an acid, above all acetic acid, or an alcohol, preferably with the addition of water, a grouping of the formula —C(=O)—O—$R_o^c$ for example by irradiation, preferably with ultraviolet light, using ultraviolet light of shorter wavelengths, for example below 290 mµ, if $R_o^c$ for example represents an arylmethyl radical which is optionally substituted in the 3-, 4- and/or 5-position, for example by lower alkoxy groups and/or nitro groups, or with ultraviolet light of longer wavelengths, for example above 290 mµ, if $R_o^c$ for example denotes an arylmethyl radical which is substituted by a nitro group in the 2-position, a grouping —C(=O)—O—$R_o^d$ or —C(=O)—O—$R_o^e$ for example by treatment with an acid agent, such as formic acid or trifluoroacetic acid, and a grouping —C(=O)—O—$R_o^f$ for example by hydrolysis, for example by treatment with a weakly acid or weakly basic agent, such as aqueous sodium bicarbonate or an aqueous potassium phosphate buffer.

In a compound of the formula XIV a grouping of the formula —C(=O)—O—$R_5^A$ can be converted into another grouping of this formula, for example a 2-bromoethoxycarbonyl group of the formula —C(=O)—O—$R_o^a$ can be converted into a 2-iodoethoxycarbonyl group by treatment with an iodine salt, such as sodium iodide, in the presence of a suitable solvent, such as acetone.

A carboxyl group which is protected by, for example silylation, can be liberated in the usual manner, for example by treatment with water or with an alcohol.

In a compound of the formula XIV having a group of the formula —C(=O)—O—$R_5$, wherein $R_5$ represents hydrogen, the free carboxyl group can be esterified in a manner which is in itself known, for example by treatment with a diazo compound, such as a diazo-lower alkane, for example diazomethane or diazoethane, or a phenyl-diazo-lower alkane, for example phenyl-diazomethane or diphenyldiazomethane, or by reaction with an alcohol suitable for esterification in the presence of an esterifying agent, such as a carbodiimide, for example dicyclohexylcarbodiimide or carbonyl-diimidazole, or in accordance with any other known and suitable esterification processes, such as reaction of a salt of the acid with a reactive ester of an alcohol and of a strong inorganic acid or of a strong organic sulphonic acid. It is furthermore possible to convert acid halides, such as acid chlorides (manufactured, for example, by treatment with oxalyl chloride), or activated esters (for example those prepared with N-hydroxy-nitrogen compounds), or mixed anhydrides (for example, those formed with halogenoformic acid lower alkyl esters, such as chloroformic acid ethyl ester, or with halogenoacetic acid halides, such as trichloroacetic acid chloride), into esters by reaction with alcohols, optionally in the presence of a base, such as pyridine.

In the above reaction stages it is possible, if necessary, transiently to protect, in a manner which is in itself known, free functional groups present in the reactants and not participating in the reaction, for example free hydroxyl, mercapto and amino groups, for example by acylation, tritylation or silylation, and free carboxyl groups, for example by esterification, including silylation, and, in each case after the reaction has taken place, to liberate these groups, if desired, in a manner which is in itself known.

The compounds of the formula XIV, especially those in which $R_1^a$ represents an acyl radical contained in pharmacologically active, naturally occurring or biosynthesisable or semisynthesisable or totally synthesisable N-acyl derivatives of 6-amino-penicillanic acid compounds or 7-amino-cephalosporanic acid compounds, $R_1^b$ denotes hydrogen, $R_5$ denotes hydrogen or an organic radical $A_5^A$ which can easily be split off under physiological conditions, and $R_4$ denotes hydrogen, are active against micro-organisms, such as Gram-positive bacteria, for example against *Staphylococcus aureus* (for example, in mice in doses of about 0.0001 to about 0.02 g/kg p.o., especially of about 0.001 to about 0.01 g/kg p.o.), and Gram-negative bacteria, for example against *Escherichia coli* (for example, in mice in doses of about 0.001 to about 0.05 g/kg p.o., especially of about 0.005 to about 0.04 g/kg p.o.), and especially also against pencillin-resistant bacteria, and can therefore, be used in the form of antibacterially active preparations.

The compounds of the formula XIV, especially those in which $R_1^a$ represents an acyl radical contained in pharmacologically active N-acyl derivates of 6-amino-penicillanic acid or 7-amino-cephalosporanic acid compounds, $R_1^b$ denotes hydrogen, $R_5$ denotes hydrogen or an organic radical $R_5^A$ which can easily be split of under physiological conditions, and $R_4$ denotes a fluoromethyl group, or salts thereof, are active against micro-organisms, such as Gram-positive bacteria, for example *Staphylococcus aureus,* inclusive penicillin-resistant bacteria of this kind, in dilutions of up to 0.000.000 1 g/ml, further against Gram-negative bacteria for example *Escherichia coli* or *Klebsiella pneumoniae,* in dilutions of up to 0.000

001 g/ml, and can therefore, be used in the form of antibacterially active preparations.

Compounds of the formula XIV, wherein $R_1{}^a$, $R_1{}^b$ and $R_5$ have the same meanings as given above for the prefered compounds of this formula, and wherein $R_4$ denotes a methyl group, and especially the compound of formula XIV wherein $R_1{}^a$ denotes the D-phenylglycyl group, $R_1{}^b$ and $R_5$ each denote hydrogen and $R_4$ denotes methyl, and their pharmacological activities are wellknown in the art [cf. USP 3 275 626, NL 68, 065 32, NL 065 33 and Ryan et al. J. Med. Chem. 12, 310 (1969)].

Compounds of the formula XIV, wherein $R_1{}^a$, $R_1{}^b$ and $R_5$ have the same meanings as given above, and wherein $R_4$ denotes a group —$CH_2R_6$, wherein $R_6$ is an organic radical, and their pharmacological properties are described in Belgian Patent No. 791 159.

The invention is described in the examples which follow.

EXAMPLE 1

A solution of 0.35 g of bis-(cis-2-oxo-3β-phenylacetylamino-4β-azetidinyl)-disulphide in 16 ml of a 9:1 mixture of acetic acid and water is treated, at about 5° C., with about 3.2 g of ethylene oxide and then with 3.5 g of zinc dust. The reaction mixture is stirred for 15 minutes at about 5° C. and for 30 minutes at room temperature and is then filtered. The filter residue is rinsed with acetone and the filtrate is evaporated. The residue is taken up in about 150 ml of ethyl acetate and the solution is washed with 50 ml of a saturated aqueous sodium bicarbonate solution and with 100 ml of a saturated aqueous sodium chloride solution, dried and evaporated. The residue, together with a crude product obtained analogously from 0.58 g of bis-(cis-2-oxo-3β-phenylacetylamino-4β-azetidinyl)-disulphide, is chromatographed on 50 g of silica gel. Using a 19:1 mixture, 4β-(2-hydroxyethylmercapto)-3β-phenylacetylamino-azetidin-2-one of the formula

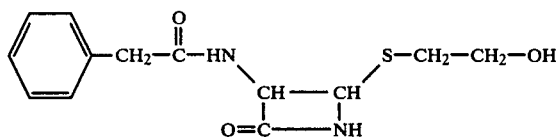

is eluted as a single product which after crystallisation from a mixture of acetone and diethyl ether melts at 141°-142° C.; $[\alpha]_D{}^{20}= +44°\pm 2°$ (c=0.571 in ethanol); thin layer chromatography (silica gel; development with iodine): Rf 0.45 (system: ethyl acetate/acetone, 1:1); infrared absorption spectrum (in mineral oil): characteristic bands at 3.01μ, 5.68μ, 6.01μ, 6.43μ and 6.52μ.

The starting material can be manufactured as follows:

15 ml of a sulphonic acid type of ion exchanger (H⊕-form) are converted into the triethylammonium salt form by treatment with a solution of 5 ml of triethylamine in 100 ml of water, the column is washed with 300 ml of water until neutral and treated with a solution of 2 g of the sodium salt of penicillin-G in 10 ml of water, and then eluted with water. A volume of 45 ml is withdrawn and lyophilised at a pressure of 0.01 mm Hg. The crude triethylammonium salt of penicillin-G, thus obtained, is dissolved in methylene chloride and the solution is dried over sodium sulphate, filtered and evaporated.

A solution of the penicillin-G triethylammonium salt thus obtainable, in a mixture of 40 ml of methylene chloride and 40 ml of tetrahydrofurane, is cooled to −10° C. and 2.9 ml of a 10 ml solution of 2 ml of chloroformic acid ethyl ester in tetrahydrofurane are slowly added, whilst stirring. The mixture is stirred for 90 minutes at −5° to 0° C., a solution of 0.395 g of sodium azide in 4 ml of water is then added, and the mixture is stirred for 30 minutes at −5° to 0° C. It is diluted with 100 ml of ice water and extracted three times with 75 ml of methylene chloride at a time; the organic extracts are washed with water, dried and evaporated at room temperature under reduced pressure. The amorphous penicillin-G azide is thus obtained, infrared absorption spectrum (in methylene chloride): characteristic bands at 3.05μ, 4.71μ, 5.62μ, 5.80μ, 5.94μ, 6.69μ and 8.50μ.

A solution of 1.72 g of the penicillin-G azide in 30 ml of benzene is treated with 1.5 ml of 2,2,2-trichloroethanol and stirred for 25 hours at 70° C. During the first 15 minutes, a steady evolution of nitrogen is observed, and after some hours the product separates out from the solution. The mixture is diluted with 60 ml of hexane whilst stirring and cooled, and is filtered after 15 minutes. The filter residue is washed with a 2:1 mixture of benzene and hexane and with cold ether. Pure 2,2-dimethyl-6β-phenylacetylamino-3-(2,2,2-trichloroethoxycarbonyl-amino)-penam is thus obtained, melting at 223°-223.5° C.; $[\alpha]_D{}^{20}= +172°$ (c=1.018 in ethanol); infrared absorption spectrum (in methylene chloride): characteristic bands at 3.04μ, 5.61μ, 5.77μ, 6.97μ, 6.70μ, 8.30μ, 9.17μ, 9.62μ and 11.85μ.

The product can also be obtained if 0.03 g of the penicillin-G azide in 2 ml of benzene are warmed to 70° C. for 20 minutes, the reaction mixture is evaporated under reduced pressure to yield 3-isocyanato-2,2-dimethyl-6β-phenyl-acetylamino-penam; infrared absorption spectrum (in methylene chloride): characteristic bands at 3.06μ, 4.48μ, 5.62μ, 5.96μ and 6.70μ; and this compound is converted, by reaction with 2,2,2-trichloroethanol, into the desired 2,2-dimethyl-6β-phenylacetylamino-3-(2,2,2-trichloroethoxycarbonyl-amino)-penam.

A solution of 11.0 g of 2.2-dimethyl-6β-phenylacetylamino-3-(2,2,2-trichloroethoxycarbonylamino)-penam in a mixture of 240 ml of anhydrous methylene chloride and 25.6 ml of pyridine is treated at −10° C., under a nitrogen atmosphere, with 166 ml of a 10% strength solution of phosphorus pentachloride in methylene chloride, and the mixture is subsequently stirred for 30 minutes at 0° C. 120 ml of absolute methanol are then added, whilst cooling strongly (−10° C.), and the mixture is stirred for a further 2 hours. 80 ml of water are added, the pH value (measured in samples diluted with water) is adjusted to 3.3 with about 9 ml of a 2 N aqueous sodium hydroxide solution, and the reaction is allowed to take place for one hour at 0° C. and for a further hour at 20° C. The mixture is then poured out onto 500 ml of a 1 M aqueous dipotassium hydrogen phosphate buffer solution, whilst stirring, and the pH value is adjusted from 6.5 to 7.0 by adding 50% strength aqueous tripotassium phosphate solution. The aqueous phase is separated off and twice washed with 200 ml of methylene chloride at a time; the three organic solutions are each twice washed with water, combined, dried over sodium sulphate and evaporated under reduced pressure. The crystalline residue is taken up in 40 ml of a 1:1 mixture of benzene and hexane; the mixture is cooled for 15 minutes at 0° C. and the precipitate is filtered off 6β-Amino-2,2-dimethyl-3-(2,2,2-trichloroethoxycarbonylamino)-penam is thus obtained, melting at 179°–180° C. (corrected); infrared absorption spectrum: characteristic bands (in methylene chloride) at 2.90μ, 5.58μ, 6.62μ, 7.17μ, 7.27μ, 8.32μ, 8.46μ, 8.82μ, 9.25μ and 9.62μ; (in Nujol) at 2.95μ, 3.01μ, 3.11μ, 5.64μ, 5.80μ, 6.35μ, 7.60μ, 7.87μ, 8.00μ, 8.27μ, 8.65μ, 8.70μ, 9.16μ and 9.57μ; thin layer chromatogram (silica gel): Rf=0.17 (in the system toluene/acetone, 8:2) and Rf=0.43 (in the system toluene/acetone 6:4); characteristic yellow colouration with ninhydrin-collidine (free amino group).

A mixture of 0.05 g of 6β-amino-2,2-dimethyl-3-(2,2,2-trichloroethoxycarbonylamino)-penam and 0.1 g of zinc dust in 2 ml of a 1:1 mixture of acetone and water is treated with 0.2 ml of acetic acid and is then vibrated at 20° C. for one hour with 45 kHz (ultrasonics), thereafter diluted with 50 ml of water. The mixture is extracted with 50 ml of ethyl acetate and the organic extract is dried over sodium sulphate and evaporated under reduced pressure. The residue is recrystallised from a mixture of methylene chloride and hexane, and 3-isopropyl-4-thia-2,6-diazabicyclo[3.2.0]heptan-7-one is thus obtained, melting point 151°–155° C.; thin layer chromatogram: Rf=0.17 (system: toluene/acetone, 8:2) and Rf=0.38 (system: toluene/acetone, 6:4).

In the above process, 0.2 g of ammonium chloride or 0.2 g of pyridine hydrochloride can be used instead of the acetic acid.

A solution of 1.64 g of 3-isopropyl-4-thia-2,6-diazabicyclo[3.2.0]heptan-7-one in 33 ml of a 1:1 mixture of acetic acid and water is treated over the course of 10 minutes with 71.7 ml of an 0.5 N solution of iodine in ethanol and the mixture is left to stand for one hour at room temperature and is then concentrated under reduced pressure. The residue, which has been dried under a high vacuum, containing bis-(cis-2-oxo-3β-amino-azetidin-4β-yl)-disulphide is suspended in 90 ml of acetonitrile and treated, at 0° C., with 4.5 ml of pyridine and 4.5 ml of phenylacetic acid chloride. The mixture is left to stand for 15 minutes at 0° C. and for one hour at room temperature and is then evaporated under reduced pressure. The residue is triturated for 30 minutes with 10 ml of a 1:1 mixture of dioxane and water and the residue is taken up in ethyl acetate; the solution is washed with a saturated aqueous sodium bicarbonate solution and a saturated aqueous sodium chloride solution, dried and evaporated. The oily residue is chromatographed on 100 g of pure silica gel; the oily bis-(cis-2-oxo-3β-phenylacetylamino-4β-azetidinyl)disulphide is eluted with a 19:1 mixture of ethyl acetate and acetone and converted into the form of a fine amorphous powder by lyophilisation; thin layer chromatogram (silica gel): Rf~0.36 (system: ethyl acetate/acetone, 1:1); infrared absorption spectrum (in potassium bromide): characteristic bands at 3.08μ, 5.62μ, 5.97μ and 6.51μ.

Bis-(cis-2-oxo-3β-phenylacetylamino-4β-azetidinyl)-disulphide can also be obtained as follows:

A solution of 0.317 g of 3,3-dimethyl-4-thia-2,6-diazabicyclo[3.2.0]heptan-7-one in 3.0 ml of methylene chloride is treated with 0.254 g of iodine in 12.0 ml of benzene; hereupon a voluminous brown precipitate immediately forms. The mixture is periodically shaken over the course of 10 minutes at room temperature and then filtered, and the filter residue is washed with benzene and pentane and suspended in 8.0 ml of acetonitrile. The suspension is treated with 2.0 ml of pyridine, whereupon a clear yellow solution is obtained which is cooled to +10° C. and treated with 0.4 ml of phenyl acetic acid chloride added dropwise, whilst stirring. The reaction mixture is left to stand for 20 minutes at room temperature and is then concentrated to a weight of 1.9 g under reduced pressure. The yellow, syrupy residue is taken up in 50 ml of ethyl acetate and the solution is washed with 50 ml of water and then evaporated. The residue is crystallised from a mixture of methanol, methylene chloride and hexane. Bis-(cis-2-oxo-3β-phenylacetylamino-4β-azetidinyl)disulphide melts at 152°–155° C. after recrystallisation from acetone and methylene chloride (analytical preparation: 156.5°–158.5° C.).

EXAMPLE 2

A mixture of 0.10 g of bis-(cis-2-oxo-3β-phenylacetylamino-4β-azetidinyl)-disulphide and 1.0 g of 1,2-propylene oxide in 5 ml of glacial acetic acid and 0.5 ml of water is treated with 1.0 g of zinc dust at 0° C. The reaction mixture is stirred for a further 30 minutes at about 0° C. and for a further 30 minutes at room temperature and is then filtered through a diatomaceous earth preparation. The residue is rinsed with acetone, and the filtrate is evaporated. The residue is taken up in 100 ml of ethyl acetate; the organic solution is washed with 50 ml of water, 50 ml of a saturated aqueous sodium bicarbonate solution and 50 ml of a saturated aqueous sodium chloride solution; the aqueous wash solutions are re-extracted with 100 ml of ethyl acetate. The combined organic solutions are dried over sodium sulphate and evaporated; the residue is chromatographed on 10 g of silica gel. Elution is carried out with ethyl acetate containing 5% of acetone, and 4β-(2-hydroxypropylmercapto)-3β-phenylacetylamino-azetidin-2-ine (sic) of the formula

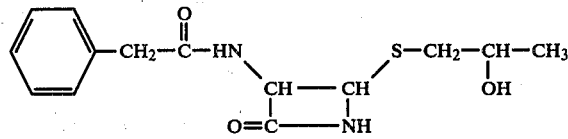

is obtained as chromatographically a single substance, which on spraying with methylene chloride crystallises and in the form of colourless crystals melts at 102°–106° C.; thin layer chromatogram (silica gel): Rf~0.44 (system: ethyl acetate/acetone, 1:1; development with iodine).

EXAMPLE 3

A mixture of 0.10 g of bis-(cis-2-oxo-3β-phenylacetylamino-4β-azetidinyl)-disulphide and 1.0 g of 1,2-butylene oxide in 5 ml of glacial acetic acid and 0.5 ml of water is treated with 1.0 g of zinc dust. The reaction mixture is stirred for 30 minutes at about 0° C. and for a further 30 minutes at room temperature and is then filtered through a diatomaceous earth preparation. The diatomaceous earth preparation is rinsed with acetone and the filtrate is evaporated. The residue is taken up in 100 ml of ethyl acetate; the organic solution is washed with 50 ml of water, a saturated aqueous sodium bicarbonate solution and 50 ml of a saturated aqueous sodium chloride solution; the aqueous wash solutions are re-extracted with 100 ml of ethyl acetate. The combined organic solutions are dried over sodium sulphate and evaporated; the residue is chromatographed on 10 g of silica gel. Elution is carried out with ethyl acetate, and with ethyl acetate containing 5% of acetone and 4β-(2-hydroxybutylmercapto)-3β-phenylacetylamino-azetidin-2-one of the formula

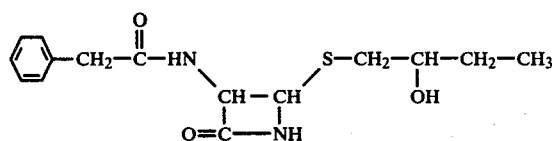

is obtained as chromatographically a single substance, which is crystallised from a mixture of methylene chloride and hexane and melts at 108°–117° C.; thin layer chromatogram (silica gel): Rf~0.49 (system: ethyl acetate/acetone, 1:1; development with iodine). According to an NMR spectrum, the substance consists of a mixture (about 1:1) of the two diastereoisomeric compounds which differ in the configuration at the carbon atom which is substituted by the hydroxyl group.

EXAMPLE 4

A solution of 0.61 g of 4β-(2-hydroxyethylmercapto)-3β-phenylacetylamino-azetidin-2-one in 10 ml of tetrahydrofurane is treated dropwise, at 0° C., with 1.38 g of chloroformic acid 2,2,2-trichloroethyl ester in 5 ml of tetrahydrofurane and then with 1.06 g of pyridine in 5 ml of tetrahydrofurane. The reaction mixture is stirred under a nitrogen atmosphere for 15 minutes at 0° C. and for 2 hours at room temperature and is then taken up in 150 ml of methylene chloride. The methylene chloride solution is washed with a saturated aqueous sodium chloride solution, dried and evaporated. The residue is chromatographed on a 50-fold quantity of silica gel; 3β-phenylacetylamino-4β-[2-(2,2,2-trichloroethoxycarbonyloxy)ethylmercapto]-azetidin-2-one of the formula

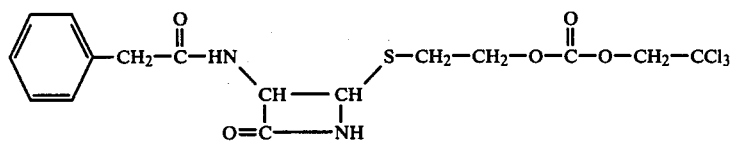

is eluted with a 1:1 mixture of methylene chloride and ethyl acetate. After crystallisation and a single recrystallisation from diethyl ether the product is obtained in the form of colourless needles, melting point 99°–101° C.; thin layer chromatogram (silica gel): Rf~0.46 (system: ethyl acetate; development with iodine); $[\alpha]_D^{20} = +3° \pm 2°$ (c=0.518 in chloroform); infrared absorption spectrum (in methylene chloride): characteristic bands at 2.88μ, 5.58μ, 5.64μ, 5.92μ and 6.62μ.

EXAMPLE 5

A solution of 5.63 g of bis-[cis-3β-(N-tert.-butoxycarbonyl-D-α-phenylglycyl)-amino-2-oxo-4β-azetidinyl]-disulphide in 190 ml of a 9:1 mixture of acetic acid and water is treated with about 60 g of ethylene oxide and 56 g of zinc dust and is stirred vigorously for one hour at room temperature. The mixture is filtered, the filtrate is concentrated, the residue is taken up in ethyl acetate, and the solution is washed with a saturated aqueous sodium bicarbonate solution and a saturated aqueous sodium chloride solution, dried over sodium sulphate and evaporated. The residue is chromatographed on 150 g of silica gel; the silica gel is eluted with ethyl acetate and 3β-N-tert.-butoxycarbonyl-D-α-phenylglycyl)-amino-4β-(2-hydroxyethylthio)azetidin-2-one of the formula

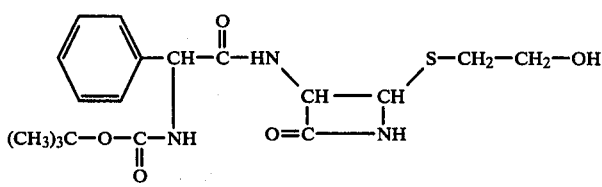

is thus obtained, melting at 130°–131° C. after crystallisation from a mixture of acetone and diethyl ether; $[\alpha]_D^{20} = -64° \pm 2°$ (c=0.622 in ethanol): thin layer chromatogram (silica gel; development with iodine vapour): Rf~0.47 (system: ethyl acetate/acetone, 1:1); infrared absorption spectrum (in methylene chloride): characteristic bands at 2.90μ, 3.00μ, 3.25μ, 3.34μ, 5.61μ, 5.83μ, 5.91μ, 6.68μ, 7.29μ, 8.58μ and 9.02μ.

EXAMPLE 6

A solution of 4.80 g of 3α-(N-tert.-butoxycarbonyl-D-α-phenylglycyl)-amino-4β-(2-hydroxyethylthio)-azetidin-2-one and 7.74 g of chloroformic acid 2,2,2-trichloroethyl ester in 100 ml of tetrahydrofurane, cooled to 0° C., is treated over the course of 10 minutes with a solution of 5.9 g of pyridine in 50 ml of tetrahydrofurane, and the mixture is stirred for 15 minutes at 0° C. and for 30 minutes at room temperature, and is concentrated. The residue is taken up in 500 ml of methylene chloride and the solution is twice washed with 100 ml of a saturated aqueous sodium chloride solution and evaporated. The residue is chromatographed on 300 ml of silica gel; elution with a 4:1 mixture of methylene chloride and ethyl acetate yields non-crystalline 3β-(N-tert.-butoxycarbonyl-D-α-phenylglycyl)-amino-4β-[2-(2,2,2-trichloroethoxycarbonyloxy)-ethylthio]azetidin-2-one of the formula

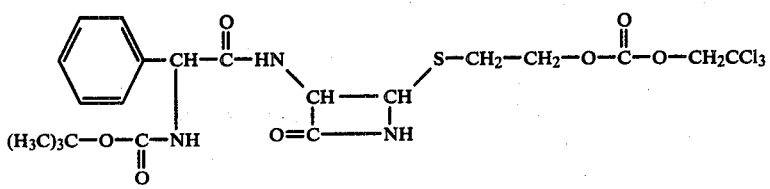

Thin layer chromatogram (silica gel; development with iodine vapour): Rf~0.55 (system: ethyl acetate) and Rf~0.19 (system: toluene/ethyl acetate, 1:1): infrared absorption spectrum (in methylene chloride): characteristic bands at 3.00μ, 3.35μ, 3.42μ, 5.61μ, 5.66μ, 5.85μ, 5.92μ, 6.75μ, 7.06μ, 8.14μ and 8.61μ.

The starting material can be obtained as follows:

A solution of 10.0 g of 3-isopropyl-4-thia-2,6-diazabicyclo[3.2.0]heptan-7-one in 200 ml of a 1:1 mixture of acetic acid and water is treated dropwise, over the course of 15 minutes, with 436 ml of an 0.2 molar solution of iodine in ethanol and after standing for one hour at room temperature the mixture is evaporated under reduced pressure. The residue, containing bis-(cis-3β-amino-2-oxo-4β-azetidinyl)disulphide, is dried in a high vacuum and is further used without purification.

The crude product obtainable according to the above process is dissolved in 200 ml of a 1:1 mixture of tetrahydrofurane and water, 8.4 ml of triethylamine are added and the whole is slowly added dropwise to a mixture, cooled to −10° C., of N-tert.-butoxycarbonyl-D-α-phenylglycine, 8.95 ml of triethylamine and 8.40 g of chloroformic acid isobutyl ester in 170 ml of tetrahydrofurane. After one hour at 0° C. and a further hour at room temperature the reaction mixture is concentrated to half and taken up in 800 ml of ethyl acetate. The solution is twice washed with 200 ml at a time of a saturated aqueous sodium bicarbonate solution and twice washed with 200 ml at a time of a saturated aqueous sodium chloride solution, dried over sodium sulphate and evaporated. The residue is chromatographed on 500 g of silica gel. Bis-[cis-3β-(N-tert.-butoxycarbonyl-D-α-phenylglycyl)-amino-2-oxo-4β-azetidinyl]-disulphide is eluted with ethyl acetate. The amorphous product melts at 163°–166° C. with decomposition; $[\alpha]_D^{20} = +145° \pm 1°$ (c=0.930 in chloroform); thin layer chromatogram (silica gel; development with iodine vapour): Rf~0.33 (system: ethyl acetate); ultraviolet absorption spectrum (in ethanol): $\lambda_{max} = 257$ mμ (ε=2,200); infrared absorption spectrum (in methylene chloride): characteristic bands at 2.90μ, 2.98μ, 3.34μ, 5.63μ, 5.90μ, 6.68μ, 7.29μ, 8.11μ, 8.58μ and 9.53μ.

EXAMPLE 7

A mixture of 0.71 g of 4β-(2-hydroxypropylthio)-3β-phenyl-acetylamino-azetidin-2-one in 25 ml of tetrahydrofurane is treated, at 0° C., with 0.72 ml of chloroformic acid 2,2,2-trichloroethyl ester and 0.83 ml of pyridine in 15 ml of tetrahydrofurane. The mixture is stirred for 30 minutes at 0° C. and for 45 minutes at room temperature, concentrated under reduced pressure to about a quarter of its volume, diluted with methylene chloride and washed with a saturated aqueous sodium chloride solution. The organic solution is dried over magnesium sulphate and evaporated under reduced pressure. The crude product is chromatographed on 90 g of silica gel, 3β-phenylacetylamino-4β-[2-(2,2,2-trichloroethoxycarbonyloxy)propylthio]-azetidin-2-one being eluted with methylene chloride and with methylene chloride containing 10% to 20% of ethyl acetate. Thin layer chromatogram (silica gel): Rf=0.53 (system: ethyl acetate); infrared absorption spectrum (in methylene chloride): characteristic bands at 3.03μ, 3.46μ, 5.62μ, 5.67μ, 5.81μ, 5.92μ and 6.70μ.

EXAMPLE 8

A mixture of 1 g of bis-[cis-3β-phenylacetylamino-2-oxo-4β-azetidinyl]-disulphide in 50 ml of acetic acid and 5 ml of water is treated with 1.1 g of 3-fluoro-1,2-propylene oxide and 10 g of zinc dust. The mixture is stirred for 1 hour at room temperature and filtered, the filtrate is concentrated and the residue is taken up in ethyl acetate. The organic solution is washed with a saturated aqueous sodium bicarbonate solution and a saturated aqueous sodium chloride solution, dried and evaporated. The crude product is chromatographed on 40 g of silica gel and 4β-(3-fluoro-2-hydroxy-propylthio)-3β-phenylacetylamino-azetidin-2-one is eluted with ethyl acetate. Thin layer chromatogram (silica gel): Rf=0.31 (system: ethyl acetate); infrared absorption spectrum (in methylene chloride): characteristic bands at 3.02μ, 3.43μ, 5.63μ, 5.90μ (broad), 6.70μ and 7.16μ.

EXAMPLE 9

A mixture of 0.330 g of 4β-(3-fluoro-2-hydroxy-propylthio)-3β-phenylacetylamino-azetidin-2-one in 20 ml of tetrahydrofurane is treated, at 0° C., with 0.495 g of chloroformic acid 2,2,2-trichloroethyl ester and thereafter dropwise with a solution of 0.370 g of pyridine in 10 ml of tetrahydrofurane. The mixture is stirred for 30 minutes at 0° C. and for 45 minutes at room temperature and filtered through a diatomaceous earth preparation, and the filtrate is evaporated to dryness under reduced pressure. The residue is taken up in 300 ml of ethyl acetate and the organic solution is washed with aqueous sodium bicarbonate solution and aqueous sodium chloride solution, dried over magnesium sulphate and evaporated. The crude product is chromatographed on 30 g of silica gel and 4β-[3-fluoro-2-(2,2,2-trichloroethoxycarbonyloxy)-propylthio]-3β-phenylacetylamino-azetidin-2-one is eluted with a 1:1 mixture of methylene chloride and ethyl acetate. Thin layer chromatogram (silica gel): Rf=0.52 (system: ethyl acetate); infrared absorption spectrum (in methylene chloride): characteristic bands at 3.02μ, 3.45μ, 5.60μ, 5.78μ, 5.92μ, 6.74μ and 7.08μ.

The compounds of the present invention can, for example, be further processed as follows:

A: A mixture of 1.0 g of 3β-phenylacetylamino-4β-[2-(2,2,2-trichloroethoxycarbonyloxy)-ethylmercapto]-azetidin-2-one and 3.0 g of glyoxylic acid tert.-butyl ester hydrate in 50 ml of benzene is boiled for 16 hours under reflux whilst separating off water, then cooled and twice washed with 25 ml of distilled water at a time, dried over sodium sulphate and evaporated. α-Hydroxy-α-{2-oxo-3β-phenylacetylamino-4β-[2-(2,2,2- trichloroethoxycarbonyloxy)-ethylmercapto]-1-azetidinyl}-acetic acid tert.-butyl ester is thus obtained, which is further processed without purification.

The crude α-hydroxy-α-{2-oxo-3β-phenylacetylamino-4β-[2-(2,2,2-trichloroethoxycarbonyloxy)-ethylmercapto]-1-azetidinyl}-acetic acid tert.-butyl ester obtainable according to the above process is dissolved in 20 ml of a 1:1 mixture of dioxane and tetrahydrofurane and treated dropwise, at −10° C., with 0.54 ml of pyridine in 2 ml of dioxane and 0.48 ml of thionyl chloride in 10 ml of a 1:1 mixture of dioxane and tetrahydrofurane. The reaction mixture is stirred for 30 minutes at −10° C. to −5° C. and for one hour under a nitrogen atmosphere, the precipitate is filtered off and the filtrate containing the α-chloro-α-{2-oxo-3β-phenylacetylamino-4β-[2-(2,2,2-trichloroethoxycarbonyloxy)-ethylmercapto]-1-azetidinyl}-acetic acid tert.-butyl ester is evaporated; the product is further processed in the crude state.

A solution of the crude α-chloro-α-{2-oxo-3β-phenylacetylamino-4β-[2-(2,2,2-trichloroethoxycarbonyloxy)-ethylmercapto]-1-azetidinyl}-acetic acid tert.-butyl ester obtainable according to the above process, in 30 ml of a 1:1 mixture of dioxane and tetrahydrofurane, is treated with 1.15 g of triphenylphosphine and 0.35 ml of pyridine and the whole is warmed at 50° C. for 2 hours and then evaporated to dryness. The residue is chromatographed on 30 g of pure silica gel, and elution with a 1:1 mixture of toluene and ethyl acetate yields α-{2-oxo-3β-phenylacetylamino-4β-[2-(2,2,2-trichloroethoxycarbonyloxy)-ethylmercapto]-1-azetidinyl}-α-triphenylphosphoranylidene-acetic acid tert.-butyl ester, which is contaminated with a little triphenylphosphine oxide and can be purified by means of preparative thin layer chromatography (silica gel; development with iodine); Rf∼0.57 (system: toluene-/acetone, 1:1); infrared absorption spectrum (in methylene chloride): characteristic bands at 3.00μ, 3.42μ, 5.68μ, 5.97μ, 6.10μ and 6.65μ.

A mixture of 0.225 g of α-{2-oxo-3β-phenylacetylamino-4β-[2-(2,2,2-trichloroethoxycarbonyloxy)-ethylmercapto]-1-azetidinyl}-α-triphenylphosphoranylidene-acetic acid tert.-butyl ester in 10 ml of a 9:1 mixture of acetic acid and water is treated with 3.0 g of zinc dust and stirred for 45 minutes at 15° C. The mixture is filtered and the filtrate is evaporated; the residue is taken up in 50 ml of ethyl acetate and the solution is washed with 25 ml of a saturated aqueous sodium bicarbonate solution and twice with 25 ml at a time of a saturated aqueous sodium chloride solution, dried over sodium sulphate and evaporated. α-[4β-(2-Hydroxy-ethylmercapto)-2-oxo-3β-phenylacetylamino-1-azetidinyl]-α-triphenylphosphoranylidene-acetic acid tert.-butyl ester is thus obtained; thin layer chromatogram (silica gel; development with iodine): Rf∼0.24 (system: toluene/acetone, 1:1).

A mixture of 0.221 g of the crude α-[4β-(2-hydroxyethylmercapto)-2-oxo-3β-phenylacetylamino-1-azetidinyl]-α-triphenylphosphoranyldiene-acetic acid tert.-butyl ester in 5 ml of dimethylsulphoxide and 5 ml of acetic anhydride is left to stand for 16 hours at room temperature and is then concentrated under reduced pressure. The residue is taken up in 100 ml of toluene; the organic solution is washed three times with 50 ml of distilled water at a time, dried over sodium sulphate and evaporated. The oily residue is chromatographed on 10 g of silica gel; the desired 7β-phenylacetylamino-ceph-3-em-4-carboxylic acid tert.-butyl ester, which forms by cyclisation from the α-(4β-formylmethylmercapto-2-oxo-3β-phenylacetylamino-1-azetidinyl)-α-triphenylphosphoranylidine-acetic acid tert.-butyl ester, obtained as an intermediate and not isolated, is eluted with a 4:1 mixture of toluene and ethyl acetate; thin layer chromatogram (silica gel): Rf∼0.48 (system: toluene/ethyl acetate, 1:1); ultraviolet absorption spectrum (in pure ethanol): $\lambda_{max}$ 258 mμ; infrared absorption spectrum (in methylene chloride): characteristic bands at 3.00μ, 3.48μ, 5.62μ, 5.81μ, 5.93μ, 6.10μ, 6.67μ, 7.15μ, 7.31μ, 7.70μ, 8.65μ and 9.03μ.

A mixture of 0.03 g of 7β-phenylacetylamino-ceph-3-em-4-carboxylic acid tert.-butyl ester and 0.5 ml of trifluoroacetic acid is left to stand for one hour at room temperature. The trifluoroacetic acid is then removed under reduced pressure and the residue is twice evaporated to dryness with 5 ml at a time of a mixture of benzene and chloroform. The residue is chromatographed on 5 g of silica gel and the 7β-phenylacetylamino-ceph-3-em-4-carboxylic acid is eluted with methylene chloride containing 5% of acetone; thin layer chromatogram (silica gel: development with iodine): Rf∼0.49 (system: n-butanol/pyridine/acetic acid/water, 40:24:6:30).

B. A mixture of 13.5 g of glyoxylic acid tert.-butyl ester hydrate in 160 ml of toluene is dehydrated by distilling off about 80 ml of toluene and is added to 5.29 g of 3β-(N-tert.-butoxycarbonyl-D-α-phenylglycyl)-amino-4β-[2-(2,2,2-trichloroethoxycarbonyloxy)-ethylthio]-azetidin-2-one, and the reaction mixture is warmed at 90° C. for 16 hours under a nitrogen atmosphere. After cooling, it is diluted with toluene to a volume of 150 ml, washed five times with 100 ml of water at a time, dried over sodium sulphate and evaporated. The residue contains α-{3β-(N-tert.-butoxycarbonyl-D-α-phenylglycyl)-amino-4β-[2-(2,2,2-trichloroethoxycarbonyloxy)-ethylthio]-2-oxo-1-azetidinyl}-α-hydroxyacetic acid tert.-butyl ester and is further processed without purification.

The oily product is dissolved in 100 ml of a 1:1 mixture of tetrahydrofurane and dioxane and at about −5° C. 2.24 ml of pyridine are added, followed by 2.00 ml of thionyl chloride, in a 1:1 mixture of tetrahydrofurane and dioxane, added over the course of 10 minutes. After standing for 30 minutes at −5° C., the cooling bath is removed; the mixture is stirred for a further hour at room temperature, filtered through a diatomaceous earth preparation and evaporated. The residue contains α-chloro-α-{3β-(N-tert.-butoxycarbonyl-D-α-phenylglycyl)-amino-4β-[2-(2,2,2-trichloroethoxycarbonyloxy)ethylthio]-2-oxo-1-azetinyl}-acetic acid tert.-butyl ester and is further processed without purification.

The above crude product is dissolved in 100 ml of a 1:1 mixture of tetrahydrofurane and dioxane, 4.86 g of triphenylphosphine and 0.75 ml of pyridine are added, and the whole is warmed at 50° C. for 10 hours under a nitrogen atmosphere. The dark red solution is concentrated, the residue is taken up in methylene chloride, and the mixture is twice washed with 100 ml of water and then evaporated. The residue is chromatographed on 200 g of silica gel, α-{3β-(N-tert.-butoxycarbonyl-D-α-phenylglycyl)-amino-4β-[2-(2,2,2-trichloroethoxycarbonyloxy)-ethylthio]-2-oxo-1-azetidinyl}-α-triphenylphosphoranylidene-acetic acid tert.-butyl ester being eluted with a 1:1 mixture of toluene and ethyl acetate; thin layer chromatogram (silica gel; development with iodine vapour): Rf∼0.25 (system: toluene-/ethyl acetate, 1:1); infrared absorption spectrum (in methylene chloride): characteristic bands at 3.00μ, 3.44μ, 5.67μ, 5.86μ, 5.92μ, 6.14μ and 6.76μ.

A solution of 1.74 g of α-{3β-(N-tert.-butoxycarbonyl-D-α-phenylglycyl)-amino-4β-[2-(2,2,2-trichloroethoxycarbonyloxy)-ethylthio]-2-oxo-1-azetidinyl}-α-triphenylphosphoranylideneacetic acid tert.-butyl ester in 65 ml of a 9:1 mixture of acetic acid and water is treated with 12 g of zinc dust and stirred for one hour at room temperature. The mixture is filtered through a diatomaceous earth preparation, the filtrate is evaporated and the residue is taken up in 500 ml of ethyl acetate. The solution is twice washed with 100 ml of a saturated aqueous sodium bicarbonate solution and with 100 ml of a saturated aqueous sodium chloride solution and the organic phase is dried over sodium sulphate and evaporated. α-[3α-(N-tert.-Butoxycarbonyl-D-α-phenylglycyl)-amino-4α-(2-hydroxyethylthio)-2-oxo-1-azetidinyl]-α-(triphenylphosphoranylidene)-acetic acid tert.-butyl ester is thus obtained. Thin layer chromatogram (silica gel; development with iodine vapour): $Rf \sim 0.29$ (system: toluene/acetone, 3:2); infrared absorption spectrum (in methylene chloride): characteristic bands at 3.00μ, 3.42μ, 5.68μ, 5.86μ, 5.93μ, 6.16μ, 6.75μ and 8.75μ.

A mixture of 1.53 g of crude α-[3α-(N-tert.-butoxycarbonyloxy-D-α-phenylglycyl)-amino-4α-(2-hydroxyethylthio)-2-oxo-1-azetidinyl]-α-(triphenylphosphoranylidene)-acetic acid tert.-butyl ester in 60 ml of a 1:1 mixture of dimethylsulphoxide and acetic anhydride is left to stand for 16 hours at room temperature under a nitrogen atmosphere and is then kept at 50° C. for a further 2 hours. The mixture is concentrated, the residue is taken up in 500 ml of toluene, and the solution is washed three times with 100 ml of water at a time. The organic phase is dried over sodium sulphate and evaporated. The residue is chromatographed on 120 g of silica gel and 7β-(N-tert.-butoxycarbonyl-D-α-phenylglycyl)-amino-ceph-3-em-4-carboxylic acid tert.-butyl ester is eluted with an 8:2 mixture of toluene and ethyl acetate. The product crystallises from a mixture of diethyl ether and pentane, melting point 159°–161° C.; $[\alpha]_D^{20} = +29° \pm 2°$ (c=0.521 in chloroform); thin layer chromatography (silica gel; development with iodine vapour): $Rf \sim 0.67$ (system: toluene/ethyl acetate, 1:1); ultraviolet absorption spectrum (in ethanol): $\lambda_{max} = 255$ mμ ($\epsilon = 5,400$); infrared absorption spectrum (in methylene chloride): characteristic bands at 2.68μ, 2.89μ, 3.33μ, 5.57μ, 5.79μ, 5.88μ, 6.08μ, 6.22μ, 6.70μ, 7.15μ, 7.28μ, 7.68μ, 8.04μ, 8.64μ, 9.05μ, 9.52μ and 9.79μ.

A mixture of 0.6367 g of 7β-(N-tert.-butoxycarbonyl-D-α-phenylglycyl)-amino-ceph-3-em-4-carboxylic acid tert.-butyl ester in 30 ml of trifluoroacetic acid is left to stand for 15 minutes at room temperature and is then treated with 100 ml of toluene and evaporated. The residue is again taken up in 100 ml of a 3:1 mixture of toluene and methanol, the solution is evaporated under reduced pressure and the residue is dried in a high vacuum. The white, pulverulent residue is dissolved in 5 ml of methanol and treated with 13 ml of a 1% strength solution of triethylamine in diethyl ether, whereupon a voluminous fresh precipitate forms. The solvent is evaporated off under reduced pressure and the residue is suspended in methylene chloride and filtered off. It is rinsed with about 150 ml of methylene chloride and dried under a high vacuum. 7β-(D-α-Phenylglycyl)-amino-ceph-3-em-4-carboxylic acid is thus obtained in the zwitter-ion form as a pale yellowish, amorphous powder. Thin layer chromatogram (silica gel; development with iodine vapour): $Rf \sim 0.29$ (system: n-butanol/pyridine/acetic acid/water, 40:24:6:30); ultraviolet absorption spectrum (in water): $\lambda_{max} = 250$ mμ ($\epsilon = 4,300$).

C. A mixture of 0.706 g of 3β-phenylacetylamino-4β-[2-(2,2,2-trichloroethoxycarbonyloxy)-propylthio]-azetidin-2-one and 2.7 g of anhydrous glyoxylic acid tert.-butyl ester in 50 ml of toluene is warmed for 16 hours at 90° C. under nitrogen and is then diluted to a volume of 300 ml with toluene. The solution is washed five times with 50 ml of water at a time, dried over sodium sulphate and evaporated under reduced pressure. The crude α-{2-oxo-3β-phenylacetylamino-4β-[2-(2,2,2-trichloroethoxycrbonyloxy)-propylthio]-1-azetidinyl}-α-hydroxyacetic acid tert.-butyl ester is further processed without purification.

A solution of 1.73 g of the crude α-{2-oxo-3β-phenylacetylamino-4β-[2-(2,2,2-trichloroethoxycarbonyloxy)-propylthio]-1-azetidinyl}-α-hydroxy-acetic acid tert.-butyl ester in 25 ml of a 1:1 mixture of tetrahydrofurane and dioxane is treated, at −5° C. and in a nitrogen atmosphere, with 0.37 ml of pyridine and 0.33 ml of thionyl chloride in 10 ml of tetrahydrofurane, and the whole is stirred for 30 minutes at −5° C. and for 1 hour at room temperature. The pyridine hydrochloride is filtered off and the filter residue is rinsed with diethyl ether. The filtrate is evaporated to dryness under reduced pressure and is dried in a high vacuum. α-Chloro-α-{2-oxo-3β-phenylacetylamino-4β-[2-(2,2,2-trichloroethoxycarbonyloxy)-propylthio]-1-azetidinyl}-acetic acid tert.-butyl ester is obtained as a dark oil and is further processed without purification.

The α-chloro-α{2-oxo-3β-phenylacetylamino-4β-[2-(2,2,2-trichloroethoxycarbonyloxy)-propylthio]-1-azetidinyl}-acetic acid tert.-butyl ester obtainable as a crude product according to the above process, in 25 ml of a 1:1 mixture of tetrahydrofurane and dioxane, is treated with 0.812 g of triphenylphosphine and 0.12 ml of pyridine and the mixture is kept at 50° C. for 10 hours. It is diluted with 300 ml of methylene chloride and the organic solution is twice washed with 100 ml of water at a time, dried over sodium sulphate and evaporated. The crude product is chromatographed on 70 g of silica gel; elution with a 1:1 mixture of toluene and ethyl acetate yields α-{2-oxo-3β-phenylacetylamino-4β-[2-(2,2,2-trichloroethoxycarbonyloxy)-propylthio]-1-azetidinyl}-α-triphenylphosphoranylidene-acetic acid tert.-butyl ester. Thin layer chromatogram (silica gel): $Rf = 0.22$ (system: toluene/ethyl acetate, 1:1); infrared absorption spectrum in methylene chloride: characteristic bands at 3.02μ, 3.45μ, 5.67μ, 5.85μ, 5.91μ, 6.15μ and 6.75μ.

A mixture of 0.562 g of α-{2-oxo-3β-phenylacetylamino-4β-[2-(2,2,2-trichloroethoxycarbonyloxy)-propylthio]-1-azetidinyl}-α-triphenylphosphoranylidene-acetic acid tert.-butyl ester in 20 ml of a 9:1 mixture of acetic acid and water is treated with 4 g of zinc dust and stirred for 1 hour at room temperature. The zinc is filtered off and rinsed with acetone, and the filtrate is evaporated to dryness under reduced pressure. The residue is taken up in 300 ml of ethyl acetate and the organic solution is twice washed with 50 ml at a time of an aqueous sodium bicarbonate solution and once with 50 ml of a saturated aqueous sodium chloride solution, dried and evaporated. α-[4β-(2-Hydroxypropylthio)-2-oxo-3β-phenylacetylamino-1-azetidinyl]-α-triphenylphosphoranylidene-acetic acid tert.-butyl ester is thus obtained, thin layer chromatogram (silica gel): Rf=0.38 (system: toluene/acetone, 1:1); infrared absorption spectrum (in methylene chloride): characteristic bands at 3.03μ, 3.44μ, 5.67μ, 5.86μ, 5.93μ, 6.17μ and 6.75μ.

A mixture of 0.150 g of the crude α-[4β-(2-hydroxy-propylthio)-2-oxo-3β-phenylacetylamino-1-azetidinyl]-α-triphenylphosphoranylidine-acetic acid tert.-butyl ester in 5 ml of dimethylsulphoxide and 5 ml of acetic anhydride is left to stand for 16 hours at room temperature and is then concentrated under reduced pressure. The residue is taken up in 100 ml of toluene; the organic solution is washed three times with 50 ml of distilled water at a time, dried over sodium sulphate and evaporated. Preparative thin layer chromatography (silica gel; system toluene/acetone 1:1) and elution of the zone visible under an ultraviolet lamp (254 nm) and having the Rf~0,36 gives the α-{4β-(2-oxo-propylthio)-2-oxo-3β-phenylacetylamino-1-azetidinyl}-α-triphenylphosphoranylidene-acetic acid tert.-butyl ester; infrared absorption spectrum (in methylene chloride): characteristic bands at 3.00μ; 5.69μ; 5.84μ; 6.15μ and 6.74μ.

A solution of 0.16 g of α-{4β-(2-oxo-propylthio)-2-oxo-3β-phenylacetylamino-1-azetidinyl}-α-triphenylphosphoranylidene-acetic acid tert.-butyl ester in 10 ml of dioxane is refluxed during 24 hours and then evaporated. The residue is taken up in ethyl acetate and washed with saturated aqueous sodium chloride solution. The organic phase is dried over sodium sulphate and evaporated. Preparative thin layer chromatography of the residue on silica gel (system: toluene/ethyl acetate 1:1) and elution of the zone visible under an ultraviolet lamp (254 nm) and having the Rf~0.45 gives the 3-methyl-7β-phenylacetylamino-ceph-3-em-4-carboxylic acid tert.-butyl ester; ultraviolet absorption spectrum (ethanol): $\lambda_{max}=269\mu$ ($\epsilon=6.500$); infrared absorption spectrum (methylene chloride): characteristic bands at 2.94μ; 5.58μ; 5.80μ; 6.10μ and 6.65μ.

A mixture of 0.04 g of 3-Methyl-7β-phenylacetylamino-ceph-3-em-4-carboxylic acid tert.-butyl ester and 1.0 ml of trifluoroacetic acid is left to stand for one hour at room temperature. The trifluoroacetic acid is then removed under reduced pressure and the residue is twice evaporated to dryness with 5 ml at a time of a mixture of benzene and chloroform. The residue is chromatographed on 5 g of silica gel and the 3-methyl-7β-phenylacetylamino-ceph-3-em-4-carboxylic acid is eluted with methylene chloride containing 5% of acetone; thin layer chromatogram (silica gel: development with iodine): (n-butanol/pyridine/acetic acid/water=40:24:6:30); ultraviolet absorption spectrum (ethanol): $\lambda_{max}=268\mu$ ($\epsilon=7200$); infrared absorption spectrum (KBr): characteristic bands at 5.63μ; 5.76μ; 5.96μ; 6.24μ; 6.54μ.

D. A mixture of 0.203 g of 4β-[3-fluoro-2-(2,2,2-trichloroethoxycarbonyloxy)-propylthio]-3β-phenylacetylaminoazetidin-2-one in 20 ml of toluene is treated with 0.730 g of anhydrous glyoxylic acid tert.-butyl ester and the whole is warmed for 15 hours in a nitrogen atmosphere at 90° C. and then diluted with 150 ml of toluene. The solution is washed five times with 30 ml of water at a time, dried over magnesium sulphate and evaporated. The crude α-{4β-[3-fluoro-2-(2,2,2-trichloroethoxycarbonyloxy)-propylthio]-2-oxo-3β-phenylacetylamino-1-azetidinyl}-α-hydroxy-acetic acid tert.-butyl ester is further processed without purification.

A mixture of 0.36 g of α-{4-β[3-fluoro-2-(2,2,2-trichloroethoxycarbonyloxy)-propylthio]-2-oxo-3β-phenylacetylamino-1-azetidinyl}-α-hydroxy-acetic acid tert.-butyl ester in 10 ml of a 1:1 mixture of tetrahydrofurane and dioxane is treated with 0.08 ml of pyridine and 0.07 ml of thionyl chloride at −5° C. and stirred for 30 minutes at −5° C. and for 1 hour at room temperature, under a nitrogen atmosphere. The pyridine hydrochloride is filtered off, the filtrate is evaporated to dryness under reduced pressure and the residue is dried in a high vacuum. The crude α-chloro-α-{4β-[3-fluoro-2-(2,2,2-trichloroethoxycarbonyloxy)-propionylthio]-2-oxo-3β-phenylacetylamino-1-azetidinyl}-acetic acid tert.-butyl ester is further processed without purification.

The crude α-chloro-α{4β-[3-fluoro-2-(2,2,2-trichloroethoxycarbonyloxy)-propylthio]-2-oxo-3β-phenylacetylamino-1-azetidinyl}-acetic acid tert.-butyl ester obtainable according to the above process is taken up in 15 ml of a mixture of tetrahydrofurane and dioxane, treated with 0.170 g of triphenylphosphine and 0.03 ml of pyridine, and warmed to 50° C. for 10 hours. The mixture is concentrated, diluted with methylene chloride and twice washed with 50 ml of water at a time. The organic phase is dried over magnesium sulphate and evaporated, and the residue is chromatographed on 15 g of silica gel. Elution with a 1:1 mixture of toluene and ethyl acetate yields α-{4β-[3-fluoro-2-(2,2,2-trichloroethoxycarbonyloxy)-propylthio]-2-oxo-3β-phenylacetylamino-1-azetidinyl}-α-triphenylphosphoranylidene-acetic acid tert.-butyl ester. Thin layer chromatogram (silica gel): Rf=0.25 (system: toluene/ethyl acetate, 1:1).

A mixture of 0.105 g of α-{4β-[3-fluoro-2-(2,2,2-trichloroethoxycarbonyloxy)-propylthio]-2-oxo-3β-phenylacetylamino-1-azetidinyl}-α-triphenylphosphoranylidene-acetic acid tert.-butyl ester in 10 ml of a 9:1 mixture of acetic acid and water is treated with 1 g of zinc dust and the mixture is kept for 45 minutes at room temperature and filtered through a diatomaceous earth preparation. The latter is rinsed with acetone, the filtrate is evaporated and the residue is taken up in ethyl acetate. The organic solution is washed with an aqueous sodium bicarbonate solution and a saturated sodium chloride solution, dried and evaporated. The residue is purified by means of preparative thin layer chromatography (silica gel; system: toluene/acetone, 1:1). The band of Rf=0.5, which is rendered visible under ultraviolet light, is scraped off and extracted with a 9:1 mixture of acetone and methanol. The extract is filtered and evaporated, and α-[4β-(3-fluoro-2-hydroxy-propylthio)-2-oxo-3β-phenylacetylamino-azetidinyl]-α-triphenylphosphoranylidene-acetic acid tert.-butyl ester is thus obtained, showing the following characteristic bands in the ultraviolet absorption spectrum (in methylene chloride): 3.00μ, 3.44μ, 5.67μ, 5.85μ (broad), 6.21μ, 6.71μ and 7.30μ.

A mixture of 53.4 mg of the crude α-[4β-(3-fluoro-2-hydroxy-propylthio)-2-oxo-3β-phenylacetylamino-1-azetidinyl]-α-triphenylphosphoranylidene-acetic acid tert.-butyl ester in 2.5 ml of dimethylsulfoxide and 2.5 ml of acetic anhydride is left to stand for 16 hours at room temperatur and is then concentrated under reduced pressure. The residue is taken up in 50 ml of toluene; the organic solution is washed with three times 25 ml of distilled water, dried over sodium sulphate and evaporated. Preparative thin layer chromatography (silica gel; system toluene/acetone 1:1) and elution of the zone visible under an ultraviolet lamp (254 nm) and having the Rf~0.34 gives the α-[4β-(3-fluoro-2-oxopropylthio)-2-oxo-3β-phenylacetylamino-1-azetidinyl]-α-triphenylphosphoranylidene-acetic acid tert.-butyl ester; infrared absorption spectrum (in methylene chloride): characteristic bands at 2.97μ; 5.68μ; 5.84μ; 6.20μ and 6.71μ.

A solution of 90 mg of α-[4β-(3-fluoro-2-oxo-propylthio)-2-oxo-3β-phenylacetylamino-1-azetidinyl]-α-triphenylphosphoranylidene-acetic acid tert.-butyl ester in 5 ml of dioxane is refluxed during 24 hours and then evaporated. The residue is taken up in ethyl acetate and washed with saturated aqueous sodium chloride solution. The organic phase is dried over sodium sulphate and evaporated. Preparative thin layer chromatography of the residue on silica gel (system: toluene/acetone 2:1) and elution of the zone visible under an ultraviolet lamp (254 um) and having the Rf∼0.49 gives the 3-fluoromethyl-7β-phenylacetylamino-ceph-3-em-4-carboxylic acid tert.-butyl ester; ultraviolet absorption spectrum (dioxan): $\lambda_{max}=262\mu$ ($\epsilon=7.100$); infrared absorption spectrum (methylene chloride): characteristic bands at 2.96μ; 5.58μ; 5.80μ; 5.94μ; 6.13μ and 6.67μ.

A mixture of 45 mg of 3-fluoromethyl-7β-phenylacetylamino-ceph-3-em-4-carboxylic acid tert.-butyl ester and 2 ml of trifluoroacetic acid is left to stand for 30 minutes at room temperatur. The trifluoroacetic acid is then removed under reduced pressure and the residue is washed with acetone/ethyl ether mixture to give 3-fluoromethyl-7β-phenylacetylamino-ceph-3-em-4-carboxylic acid as an amorphous powder; thin layer chromatogram on silica gel (system: chloroform/methanol 1:1): Rf∼0.50; ultraviolet absorption spectrum (ethanol): $\lambda_{max}$: 259μ ($\epsilon=5300$); infrared absorption spectrum (nujol): characteristic bands at 3.02μ; 5.60μ; 5.78μ; 6.06μ and 6.51μ.

We claim:
1. 4β-(2-hydroxypropylthio)-3β-phenylacetylamino-azetidin-2-one.

* * * * *